United States Patent
Armstrong et al.

(10) Patent No.: US 11,783,943 B2
(45) Date of Patent: Oct. 10, 2023

(54) REDUCED PRESSURE THERAPY DEVICE OPERATION AND AUTHORIZATION MONITORING

(71) Applicant: Smith & Nephew, Inc., Memphis, TN (US)

(72) Inventors: Edward Armstrong, Palm Harbor, FL (US); Carrie Lee Childress, Dallas, TX (US); Tim Warren Dana, Seminole, FL (US); William W. Gregory, Gainesville, FL (US); William Joseph Jaecklein, Saint Petersburg, FL (US); Michael Mosholder, Palm Harbor, FL (US); Felix C. Quintanar, Hull (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/703,145

(22) Filed: Mar. 24, 2022

(65) Prior Publication Data

US 2022/0215946 A1    Jul. 7, 2022

Related U.S. Application Data

(62) Division of application No. 15/766,213, filed as application No. PCT/US2015/057211 on Oct. 23, 2015, now Pat. No. 11,315,681.

(Continued)

(51) Int. Cl.
G06Q 40/06 (2012.01)
G06Q 40/04 (2012.01)
(Continued)

(52) U.S. Cl.
CPC .............. *G16H 40/63* (2018.01); *A61M 1/96* (2021.05); *G16H 40/67* (2018.01); *A61M 1/962* (2021.05);
(Continued)

(58) Field of Classification Search
CPC ......... G16H 40/63; G16H 40/67; G16H 20/40
See application file for complete search history.

(56) References Cited

U.S. PATENT DOCUMENTS

| 695,270 A | 3/1902 | Beringer |
| 3,194,239 A | 7/1965 | Sullivan et al. |

(Continued)

FOREIGN PATENT DOCUMENTS

| CA | 2819475 A1 * | 6/2012 | ......... A61B 5/14557 |
| CN | 201921164 U | 8/2011 | |

(Continued)

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.

(Continued)

*Primary Examiner* — Guy K Townsend
(74) *Attorney, Agent, or Firm* — Knobbe, Martens Olson & Bear, LLP

(57) ABSTRACT

Embodiments of a negative pressure wound therapy systems and methods for operating the systems are disclosed. In some embodiments, a system includes a pump assembly, canister, and a wound dressing configured to be positioned over a wound. The pump assembly, canister, and the wound dressing can be fluidically connected to facilitate delivery of negative pressure to a wound. The pump assembly can be configured to communicate data to a remote computer. The data can include location information, usage information, (Continued)

therapy information, and the like. Remote management and tracking of the pump assembly can be performed.

15 Claims, 10 Drawing Sheets

Related U.S. Application Data

(60) Provisional application No. 62/238,501, filed on Oct. 7, 2015.

(51) Int. Cl.
  *G06N 5/04* (2023.01)
  *G06N 20/00* (2019.01)
  *A61M 1/00* (2006.01)
  *G16H 40/63* (2018.01)
  *G16H 40/67* (2018.01)
  *G16H 20/40* (2018.01)

(52) U.S. Cl.
  CPC ..... *A61M 1/982* (2021.05); *A61M 2205/3561* (2013.01); *A61M 2205/3584* (2013.01); *A61M 2205/505* (2013.01); *A61M 2205/52* (2013.01); *G16H 20/40* (2018.01)

(56) References Cited

U.S. PATENT DOCUMENTS

| | | | |
|---|---|---|---|
| 4,832,299 A | 5/1989 | Gorton et al. |
| 5,219,428 A | 6/1993 | Stern |
| 5,473,536 A | 12/1995 | Wimmer |
| 5,622,429 A | 4/1997 | Heinze |
| 5,960,403 A | 9/1999 | Brown |
| 6,055,506 A | 4/2000 | Frasca et al. |
| 6,336,900 B1 | 1/2002 | Alleckson et al. |
| 6,353,445 B1 | 3/2002 | Babula et al. |
| 6,375,614 B1 | 4/2002 | Braun et al. |
| 6,385,622 B2 | 5/2002 | Bouve et al. |
| 6,406,426 B1 | 6/2002 | Reuss et al. |
| 6,434,572 B2 | 8/2002 | Derzay et al. |
| 6,460,041 B2 | 10/2002 | Lloyd |
| 6,574,518 B1 | 6/2003 | Lounsberry et al. |
| 6,640,145 B2 | 10/2003 | Hoffberg et al. |
| 6,640,246 B1 | 10/2003 | Gary et al. |
| 6,675,131 B2 | 1/2004 | Hahn |
| 6,681,003 B2 | 1/2004 | Linder et al. |
| 6,723,046 B2 | 4/2004 | Lichtenstein et al. |
| 6,747,556 B2 | 6/2004 | Medema et al. |
| 6,779,024 B2 | 8/2004 | DeLaHUERGA |
| 6,782,285 B2 | 8/2004 | Birkenbach et al. |
| 6,868,528 B2 | 3/2005 | Roberts |
| 6,871,211 B2 | 3/2005 | Labounty et al. |
| 6,909,974 B2 | 6/2005 | Yung et al. |
| 6,912,481 B2 | 6/2005 | Breunissen et al. |
| 6,961,731 B2 | 11/2005 | Holbrook |
| 7,004,915 B2 | 2/2006 | Boynton et al. |
| 7,022,113 B2 | 4/2006 | Lockwood et al. |
| 7,051,012 B2 | 5/2006 | Cole et al. |
| 7,062,251 B2 | 6/2006 | Birkett et al. |
| 7,066,883 B2 | 6/2006 | Schmidt et al. |
| 7,103,578 B2 | 9/2006 | Beck et al. |
| 7,108,683 B2 | 9/2006 | Zamierowski |
| 7,120,488 B2 | 10/2006 | Nova et al. |
| 7,133,869 B2 | 11/2006 | Bryan et al. |
| 7,167,858 B2 | 1/2007 | Naeymi-Rad et al. |
| 7,212,829 B1 | 5/2007 | Lau et al. |
| 7,264,591 B2 | 9/2007 | Brown |
| 7,304,573 B2 | 12/2007 | Postma |
| 7,311,665 B2 | 12/2007 | Hawthorne et al. |
| 7,333,002 B2 | 2/2008 | Bixler et al. |
| 7,353,179 B2 | 4/2008 | Ott et al. |
| 7,384,267 B1 | 6/2008 | Franks et al. |
| 7,430,598 B2 | 9/2008 | Raden et al. |
| 7,438,705 B2 | 10/2008 | Karpowicz et al. |
| 7,451,002 B2 | 11/2008 | Choubey |
| 7,457,804 B2 | 11/2008 | Uber et al. |
| 7,460,872 B2 | 12/2008 | Millard et al. |
| 7,534,240 B1 | 5/2009 | Johnson |
| 7,598,855 B2 | 10/2009 | Scalisi et al. |
| 7,608,066 B2 | 10/2009 | Vogel |
| 7,627,334 B2 | 12/2009 | Cohen et al. |
| 7,649,449 B2 | 1/2010 | Fenske et al. |
| 7,670,323 B2 | 3/2010 | Hunt et al. |
| 7,671,733 B2 | 3/2010 | McNeal et al. |
| 7,684,999 B2 | 3/2010 | Brown |
| 7,723,560 B2 | 5/2010 | Lockwood et al. |
| 7,734,764 B2 | 6/2010 | Weiner et al. |
| 7,749,164 B2 | 7/2010 | Davis |
| 7,779,153 B2 | 8/2010 | Van den Heuvel et al. |
| 7,789,828 B2 | 9/2010 | Clapp |
| 7,794,438 B2 | 9/2010 | Henley et al. |
| 7,827,148 B2 | 11/2010 | Mori et al. |
| 7,846,141 B2 | 12/2010 | Weston |
| 7,862,339 B2 | 1/2011 | Mulligan |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,912,823 B2 | 3/2011 | Ferrari et al. |
| 7,925,603 B1 | 4/2011 | Laidig et al. |
| 7,933,817 B2 | 4/2011 | Radl et al. |
| 7,976,519 B2 | 7/2011 | Bubb et al. |
| 7,981,098 B2 | 7/2011 | Boehringer et al. |
| 7,988,850 B2 | 8/2011 | Roncadi et al. |
| 8,015,443 B2 | 9/2011 | Adachi |
| 8,015,972 B2 | 9/2011 | Pirzada |
| 8,019,618 B2 | 9/2011 | Brown |
| 8,054,950 B1 | 11/2011 | Hung et al. |
| 8,094,009 B2 | 1/2012 | Allen et al. |
| 8,126,735 B2 | 2/2012 | Dicks et al. |
| 8,130,095 B2 | 3/2012 | Allen et al. |
| 8,131,472 B2 | 3/2012 | Chow et al. |
| 8,180,750 B2 | 5/2012 | Wilmering et al. |
| 8,190,445 B2 | 5/2012 | Kuth et al. |
| 8,190,448 B2 | 5/2012 | Bajars et al. |
| 8,228,188 B2 | 7/2012 | Key et al. |
| 8,246,606 B2 | 8/2012 | Stevenson et al. |
| 8,249,894 B2 | 8/2012 | Brown |
| 8,255,241 B2 | 8/2012 | Cafer |
| 8,260,630 B2 | 9/2012 | Brown |
| 8,280,682 B2 | 10/2012 | Vock et al. |
| 8,284,046 B2 | 10/2012 | Allen et al. |
| 8,290,792 B2 | 10/2012 | Sekura |
| 8,291,337 B2 | 10/2012 | Gannin et al. |
| 8,323,263 B2 | 12/2012 | Wood et al. |
| 8,332,233 B2 | 12/2012 | Ott et al. |
| 8,334,768 B2 | 12/2012 | Eaton et al. |
| 8,337,482 B2 | 12/2012 | Wood et al. |
| 8,360,975 B1 | 1/2013 | Schwieterman et al. |
| 8,400,295 B1 | 3/2013 | Khaira |
| 8,409,160 B2 | 4/2013 | Locke et al. |
| 8,422,377 B2 | 4/2013 | Weiner et al. |
| 8,424,517 B2 | 4/2013 | Sutherland et al. |
| 8,436,871 B2 | 5/2013 | Alberte |
| 8,439,882 B2 | 5/2013 | Kelch |
| 8,457,740 B2 | 6/2013 | Osche |
| 8,480,641 B2 | 7/2013 | Jacobs |
| 8,515,776 B2 | 8/2013 | Schoenberg |
| 8,532,764 B2 | 9/2013 | Duke |
| 8,535,296 B2 | 9/2013 | Blott et al. |
| 8,540,688 B2 | 9/2013 | Eckstein et al. |
| 8,545,483 B2 | 10/2013 | Schwabe et al. |
| 8,554,195 B2 | 10/2013 | Rao |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,626,342 B2 | 1/2014 | Williams et al. |
| 8,626,526 B2 | 1/2014 | Lemke et al. |
| 8,632,485 B2 | 1/2014 | Schlaeper et al. |
| 8,641,693 B2 | 2/2014 | Locke et al. |
| 8,659,420 B2 | 2/2014 | Salvat et al. |
| 8,668,677 B2 | 3/2014 | Eckstein et al. |

(56) References Cited

U.S. PATENT DOCUMENTS

| | | |
|---|---|---|
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,781,847 B2 | 7/2014 | Simms et al. |
| 8,791,316 B2 | 7/2014 | Greener |
| 8,795,171 B2 | 8/2014 | Adamczyk |
| 8,795,244 B2 | 8/2014 | Randolph et al. |
| 8,838,136 B2 | 9/2014 | Carnes et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,943,168 B2 | 1/2015 | Wiesner et al. |
| 8,945,073 B2 | 2/2015 | Croizat et al. |
| 8,947,237 B2 | 2/2015 | Margon et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 * | 6/2015 | Buan ................ G16H 20/40 |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 * | 8/2015 | Bennett ................ G16H 40/67 |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,220,822 B2 | 12/2015 | Hartwell |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,424,020 B2 | 8/2016 | Borges et al. |
| 9,427,159 B2 | 8/2016 | Chang |
| 9,436,645 B2 | 9/2016 | Al-Ali et al. |
| 9,436,800 B2 | 9/2016 | Forrester |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,602,952 B2 | 3/2017 | Kang et al. |
| 9,628,460 B2 | 4/2017 | Leong et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,716,757 B2 | 7/2017 | Fernandes |
| 9,740,825 B2 | 8/2017 | Sansale et al. |
| 9,741,084 B2 | 8/2017 | Holmes et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,864,066 B2 | 1/2018 | Park et al. |
| 9,871,866 B2 | 1/2018 | Borges et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | DeBusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,127,357 B2 | 11/2018 | Whiting et al. |
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 * | 6/2019 | Deutsch ................ A61M 1/98 |
| 10,537,657 B2 | 1/2020 | Phillips et al. |
| 11,147,459 B2 * | 10/2021 | Sobol ................ H04W 4/80 |
| 11,315,681 B2 * | 4/2022 | Armstrong ............ A61M 1/96 |
| 11,426,506 B2 * | 8/2022 | Moore ................ G16H 40/63 |
| 2001/0013822 A1 | 8/2001 | Nazarian et al. |
| 2001/0031944 A1 | 10/2001 | Peterson et al. |
| 2002/0013516 A1 | 1/2002 | Freyre et al. |
| 2002/0013545 A1 | 1/2002 | Soltanpour et al. |
| 2002/0049562 A1 | 4/2002 | Hahn |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0161317 A1 | 10/2002 | Risk et al. |
| 2002/0177757 A1 | 11/2002 | Britton |
| 2002/0184055 A1 | 12/2002 | Naghavi et al. |
| 2002/0193679 A1 | 12/2002 | Malave et al. |
| 2003/0009244 A1 | 1/2003 | Engleson et al. |
| 2003/0018736 A1 | 1/2003 | Christ et al. |
| 2003/0105389 A1 | 6/2003 | Noonan et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0019464 A1 | 1/2004 | Martucci et al. |
| 2004/0039255 A1 | 2/2004 | Simonsen et al. |
| 2004/0054775 A1 | 3/2004 | Poliac et al. |
| 2004/0064132 A1 | 4/2004 | Boehringer et al. |
| 2004/0068224 A1 | 4/2004 | Couvillon, Jr. et al. |
| 2004/0078223 A1 | 4/2004 | Sacco et al. |
| 2004/0143458 A1 | 7/2004 | Pulkkinen et al. |
| 2004/0167802 A1 | 8/2004 | Takada et al. |
| 2004/0167804 A1 | 8/2004 | Simpson et al. |
| 2004/0171982 A1 | 9/2004 | Danchin |
| 2004/0172301 A1 | 9/2004 | Mihai et al. |
| 2004/0181314 A1 | 9/2004 | Zaleski |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065471 A1 | 3/2005 | Kuntz |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0256447 A1 | 11/2005 | Richardson et al. |
| 2005/0261805 A1 | 11/2005 | Mori et al. |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0064491 A1 | 3/2006 | Ebert et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |

(56) References Cited

U.S. PATENT DOCUMENTS

| | | |
|---|---|---|
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0224051 A1 | 10/2006 | Teller et al. |
| 2006/0229557 A1 | 10/2006 | Fathallah et al. |
| 2006/0246922 A1 | 11/2006 | Gasbarro et al. |
| 2006/0255935 A1 | 11/2006 | Scalisi et al. |
| 2007/0136099 A1 | 6/2007 | Neligh et al. |
| 2007/0156456 A1 | 7/2007 | Mcgillin et al. |
| 2007/0197881 A1 | 8/2007 | Wolf et al. |
| 2007/0219480 A1 | 9/2007 | Kamen et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0005000 A1 | 1/2008 | Radl et al. |
| 2008/0009681 A1 | 1/2008 | Al Hussiny |
| 2008/0041401 A1 | 2/2008 | Casola et al. |
| 2008/0071209 A1 | 3/2008 | Moubayed et al. |
| 2008/0071234 A1 | 3/2008 | Kelch et al. |
| 2008/0086357 A1 | 4/2008 | Choubey et al. |
| 2008/0091175 A1 | 4/2008 | Frikart et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | Dehaan |
| 2008/0221396 A1 | 9/2008 | Garces et al. |
| 2008/0241396 A1 | 10/2008 | Dresser |
| 2008/0242945 A1 | 10/2008 | Gugliotti et al. |
| 2008/0312953 A1 | 12/2008 | Claus |
| 2009/0037216 A1 | 2/2009 | Bluemler et al. |
| 2009/0037220 A1 | 2/2009 | Chambers et al. |
| 2009/0043268 A1 | 2/2009 | Eddy et al. |
| 2009/0048492 A1 | 2/2009 | Rantala et al. |
| 2009/0048865 A1 | 2/2009 | Breazeale, Jr. |
| 2009/0097623 A1 | 4/2009 | Bharadwaj |
| 2009/0099866 A1 | 4/2009 | Newman |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0182594 A1 | 7/2009 | Choubey |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0206017 A1 | 8/2009 | Rohde et al. |
| 2009/0224889 A1 | 9/2009 | Aggarwal et al. |
| 2009/0254362 A1 | 10/2009 | Choubey et al. |
| 2009/0270833 A1 | 10/2009 | DeBelser et al. |
| 2009/0281464 A1 | 11/2009 | Cioanta et al. |
| 2009/0281822 A1 | 11/2009 | Warner et al. |
| 2009/0281830 A1 | 11/2009 | Mcnames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 1/2010 | Blowers et al. |
| 2010/0036333 A1* | 2/2010 | Schenk, III ............ A61M 1/982 604/313 |
| 2010/0056875 A1 | 3/2010 | Schoenberg et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0114026 A1 | 5/2010 | Karratt et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0003610 A1 | 1/2011 | Key et al. |
| 2011/0004188 A1 | 1/2011 | Shekalim |
| 2011/0009824 A1 | 1/2011 | Yodfat et al. |
| 2011/0028881 A1 | 2/2011 | Basaglia |
| 2011/0028882 A1 | 2/2011 | Basaglia |
| 2011/0034861 A1 | 2/2011 | Schaefer |
| 2011/0040288 A1 | 2/2011 | Eckstein et al. |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0092958 A1* | 4/2011 | Jacobs ................ A61M 1/96 604/543 |
| 2011/0106561 A1 | 5/2011 | Eaton, Jr. et al. |
| 2011/0112857 A1 | 5/2011 | Yurko et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123796 A1 | 5/2012 | Mcfaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0197196 A1 | 8/2012 | Halbert et al. |
| 2012/0212455 A1 | 8/2012 | Kloeffel |
| 2012/0215455 A1 | 8/2012 | Patil et al. |
| 2012/0226768 A1 | 9/2012 | Gaines et al. |
| 2012/0259651 A1 | 10/2012 | Mallon et al. |
| 2012/0271256 A1 | 10/2012 | Locke et al. |
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0302978 A1* | 11/2012 | Buan ................ G06Q 30/06 604/319 |
| 2012/0310205 A1 | 12/2012 | Lee et al. |
| 2013/0018355 A1 | 1/2013 | Brand et al. |
| 2013/0023719 A1* | 1/2013 | Bennett ................ A61B 5/0002 601/149 |
| 2013/0035615 A1 | 2/2013 | Hsieh |
| 2013/0045764 A1 | 2/2013 | Vik et al. |
| 2013/0062265 A1 | 3/2013 | Balschat et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0133036 A1 | 5/2013 | Wang et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0165821 A1 | 6/2013 | Freedman et al. |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |

(56) References Cited

U.S. PATENT DOCUMENTS

| | | |
|---|---|---|
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0291060 A1* | 10/2013 | Moore ............... G06F 21/6254 726/1 |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0018637 A1* | 1/2014 | Bennett ............... H04L 43/0817 607/51 |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0055588 A1 | 2/2014 | Bangera et al. |
| 2014/0058344 A1* | 2/2014 | Toth ...................... A61B 5/412 604/319 |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0136218 A1 | 5/2014 | Bolene et al. |
| 2014/0148138 A1 | 5/2014 | Chou |
| 2014/0171753 A1 | 6/2014 | Montejo et al. |
| 2014/0187888 A1 | 7/2014 | Hatziantoniou |
| 2014/0207090 A1 | 7/2014 | Jian |
| 2014/0222446 A1 | 8/2014 | Ash et al. |
| 2014/0235975 A1 | 8/2014 | Carnes |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0316819 A1 | 10/2014 | Dunsirn et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0095068 A1 | 4/2015 | Ryan et al. |
| 2015/0100340 A1 | 4/2015 | Folsom et al. |
| 2015/0112707 A1 | 4/2015 | Manice et al. |
| 2015/0112725 A1 | 4/2015 | Ryan |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0120328 A1 | 4/2015 | Ryan et al. |
| 2015/0133829 A1* | 5/2015 | DeBusk ............ A61F 13/00068 601/6 |
| 2015/0143300 A1 | 5/2015 | Zhang et al. |
| 2015/0159066 A1 | 6/2015 | Hartwell et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227712 A1 | 8/2015 | Ryan et al. |
| 2015/0227716 A1 | 8/2015 | Ryan et al. |
| 2015/0227717 A1 | 8/2015 | Ryan et al. |
| 2015/0228043 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0257643 A1 | 9/2015 | Watson et al. |
| 2015/0261920 A1 | 9/2015 | Blick |
| 2015/0269323 A1 | 9/2015 | Ginsburg |
| 2015/0286970 A1 | 10/2015 | Dickerson et al. |
| 2015/0304478 A1 | 10/2015 | Kim et al. |
| 2015/0310182 A1 | 10/2015 | Henze et al. |
| 2015/0324943 A1 | 11/2015 | Han et al. |
| 2015/0339445 A1 | 11/2015 | Gruby et al. |
| 2015/0363058 A1 | 12/2015 | Chung et al. |
| 2015/0370984 A1 | 12/2015 | Russell et al. |
| 2015/0370997 A1 | 12/2015 | Krongrad et al. |
| 2015/0379441 A1 | 12/2015 | Syed et al. |
| 2016/0004820 A1* | 1/2016 | Moore .................. G16H 15/00 705/3 |
| 2016/0004824 A1 | 1/2016 | Stanton et al. |
| 2016/0018963 A1 | 1/2016 | Robbins et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0058286 A1 | 3/2016 | Joshua et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0085415 A1 | 3/2016 | Humphrys et al. |
| 2016/0098524 A1 | 4/2016 | Himmelstein |
| 2016/0110507 A1 | 4/2016 | Abbo |
| 2016/0110985 A1 | 4/2016 | Lee et al. |
| 2016/0128571 A1 | 5/2016 | Adler |
| 2016/0129186 A1 | 5/2016 | Douglas et al. |
| 2016/0135752 A1 | 5/2016 | Beaumont |
| 2016/0136339 A1* | 5/2016 | Begin ..................... A61M 1/98 604/319 |
| 2016/0142443 A1 | 5/2016 | Ting et al. |
| 2016/0151015 A1 | 6/2016 | Condurso et al. |
| 2016/0154936 A1 | 6/2016 | Kalathil |
| 2016/0154943 A1 | 6/2016 | Cho et al. |
| 2016/0171866 A1 | 6/2016 | Dupasquier et al. |
| 2016/0180031 A1 | 6/2016 | Slater |
| 2016/0184497 A1 | 6/2016 | Phillips et al. |
| 2016/0196399 A1 | 7/2016 | Bonhomme |
| 2016/0203275 A1 | 7/2016 | Benjamin et al. |
| 2016/0203283 A1 | 7/2016 | Baruah et al. |
| 2016/0209837 A1 | 7/2016 | Kim |
| 2016/0212577 A1 | 7/2016 | Dor et al. |
| 2016/0217433 A1 | 7/2016 | Walton et al. |
| 2016/0246943 A1 | 8/2016 | Lake et al. |
| 2016/0260035 A1 | 9/2016 | Crooks et al. |
| 2016/0287189 A1 | 10/2016 | Modai et al. |
| 2016/0308969 A1 | 10/2016 | Aihara et al. |
| 2016/0321404 A1 | 11/2016 | Ginsburg |
| 2016/0321422 A1 | 11/2016 | Albright |
| 2017/0004106 A1 | 1/2017 | Joshua et al. |
| 2017/0004271 A1 | 1/2017 | Ash et al. |

(56) References Cited

U.S. PATENT DOCUMENTS

| | | |
|---|---|---|
| 2017/0007494 A1 | 1/2017 | Rock et al. |
| 2017/0014028 A1 | 1/2017 | Clear, Jr. |
| 2017/0017765 A1 | 1/2017 | Yegge et al. |
| 2017/0032648 A1 | 2/2017 | Mcclain et al. |
| 2017/0046503 A1 | 2/2017 | Cho et al. |
| 2017/0053073 A1 | 2/2017 | Allen et al. |
| 2017/0055205 A1 | 2/2017 | Morris et al. |
| 2017/0068781 A1 | 3/2017 | Zasowski et al. |
| 2017/0074717 A1 | 3/2017 | Pilkington et al. |
| 2017/0078396 A1 | 3/2017 | Haas et al. |
| 2017/0116373 A1 | 4/2017 | Ginsburg et al. |
| 2017/0150939 A1 | 6/2017 | Shah |
| 2017/0173262 A1* | 6/2017 | Veltz .................. G16H 20/17 |
| 2017/0212995 A1 | 7/2017 | Ingmanson |
| 2017/0220755 A1* | 8/2017 | Fowler ................ G06Q 10/087 |
| 2017/0270533 A1 | 9/2017 | Barton et al. |
| 2017/0273116 A1 | 9/2017 | Elghazzawi |
| 2017/0327371 A1 | 11/2017 | Bai et al. |
| 2018/0004908 A1 | 1/2018 | Barrus et al. |
| 2018/0052454 A1 | 2/2018 | Magno et al. |
| 2018/0089387 A1 | 3/2018 | Swank |
| 2018/0092774 A1* | 4/2018 | Mehta ..................... A61B 3/16 |
| 2018/0096292 A1* | 4/2018 | DeBusk ............ G06K 7/10316 |
| 2018/0139572 A1 | 5/2018 | Hansen |
| 2018/0144817 A1 | 5/2018 | Lofgren et al. |
| 2018/0158545 A1 | 6/2018 | Blomquist |
| 2018/0160907 A1* | 6/2018 | Verma ................ A61B 1/00016 |
| 2018/0224559 A1 | 8/2018 | Park et al. |
| 2018/0233016 A1 | 8/2018 | Daniel et al. |
| 2018/0233221 A1 | 8/2018 | Blomquist |
| 2018/0234499 A1 | 8/2018 | Borges et al. |
| 2018/0247713 A1* | 8/2018 | Rothman .......... A61B 5/02055 |
| 2018/0308578 A1* | 10/2018 | Armstrong ............. A61M 1/96 |
| 2018/0375849 A1* | 12/2018 | Koskimies ............ H04L 9/3234 |
| 2019/0057189 A1* | 2/2019 | Frederickson ........ A61B 5/1112 |
| 2019/0083353 A1* | 3/2019 | Khurana ............. A61H 9/0092 |
| 2019/0147721 A1* | 5/2019 | Avitan .................. G06F 1/3209 |
| | | 340/573.1 |
| 2019/0209022 A1* | 7/2019 | Sobol .................. A61B 5/0022 |
| 2019/0213352 A1* | 7/2019 | Rios ...................... A61M 1/96 |
| 2019/0328943 A1* | 10/2019 | Deutsch .................. A61M 1/74 |
| 2020/0078499 A1* | 3/2020 | Gadde .................. A61B 5/4836 |
| 2020/0222599 A1* | 7/2020 | Gregory ................ A61M 1/98 |
| 2020/0306422 A1* | 10/2020 | Moore .................... A61M 1/73 |
| 2021/0174448 A1* | 6/2021 | Kotarinos .............. G06Q 40/04 |
| 2021/0196869 A1* | 7/2021 | Hartwell .................. G16H 10/60 |
| 2021/0379272 A1* | 12/2021 | Hartwell .................. G16H 40/60 |
| 2021/0401358 A1* | 12/2021 | Quintanar ............... G16H 20/30 |
| 2022/0189620 A1* | 6/2022 | Quintanar ............... G16H 40/67 |
| 2022/0215946 A1* | 7/2022 | Armstrong ............. A61M 1/96 |
| 2022/0249293 A1* | 8/2022 | Lin ..................... A61F 13/0216 |
| 2022/0362454 A1* | 11/2022 | Moore .................... A61M 1/96 |

FOREIGN PATENT DOCUMENTS

| | | |
|---|---|---|
| CN | 102805894 A | 12/2012 |
| CN | 102961815 A | 3/2013 |
| CN | 104721892 A | 6/2015 |
| DE | 102010036405 A1 | 1/2012 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |
| EP | 1684146 A2 | 7/2006 |
| EP | 1788503 A2 | 5/2007 |
| EP | 1839244 A1 | 10/2007 |
| EP | 1839615 A1 | 10/2007 |
| EP | 1857950 A2 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2172859 A1 | 4/2010 |
| EP | 2214552 A1 | 8/2010 |
| EP | 2218478 A1 | 8/2010 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2366721 A1 | 9/2011 |
| EP | 2384472 A1 | 11/2011 |
| EP | 2226002 B1 | 1/2012 |
| EP | 1610494 B1 | 3/2012 |
| EP | 1248660 B1 | 4/2012 |
| EP | 2023800 B1 | 4/2012 |
| EP | 2441409 A1 | 4/2012 |
| EP | 2451513 A1 | 5/2012 |
| EP | 1248661 B1 | 8/2012 |
| EP | 2488977 A1 | 8/2012 |
| EP | 2562665 A2 | 2/2013 |
| EP | 2619723 A2 | 7/2013 |
| EP | 1881784 B1 | 10/2013 |
| EP | 2664194 A2 | 11/2013 |
| EP | 2743850 A2 | 6/2014 |
| EP | 2745204 A1 | 6/2014 |
| EP | 2795492 A1 | 10/2014 |
| EP | 2841895 A1 | 3/2015 |
| EP | 2850771 A1 | 3/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2945084 A1 | 11/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3010398 A1 | 4/2016 |
| EP | 3054389 A2 | 8/2016 |
| EP | 3070628 A1 | 9/2016 |
| EP | 3078010 A1 | 10/2016 |
| EP | 3096113 A1 | 11/2016 |
| EP | 2563437 B1 | 3/2017 |
| EP | 3134854 A1 | 3/2017 |
| EP | 3027242 B1 | 4/2017 |
| EP | 2556650 B1 | 5/2017 |
| EP | 3174569 A1 | 6/2017 |
| EP | 2632407 B1 | 8/2017 |
| EP | 3209358 A1 | 8/2017 |
| EP | 3041571 B1 | 9/2017 |
| EP | 2856767 B1 | 11/2017 |
| EP | 2320971 B1 | 5/2018 |
| EP | 2335173 B1 | 5/2018 |
| EP | 3100188 B1 | 6/2018 |
| EP | 2440112 B1 | 10/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 2881875 B1 | 5/2019 |
| EP | 2836269 B1 | 8/2019 |
| EP | 2866851 B1 | 9/2019 |
| GB | 2409951 A | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 A | 5/2011 |
| GB | 2488904 A | 9/2012 |
| GB | 2446923 B | 5/2013 |

(56) References Cited

FOREIGN PATENT DOCUMENTS

| | | | | |
|---|---|---|---|---|
| GB | 2499986 | A | 9/2013 | |
| GB | 2491946 | B | 8/2014 | |
| GB | 2499873 | B | 5/2016 | |
| GB | 2533910 | A | 7/2016 | |
| GB | 2541286 | A | 2/2017 | |
| WO | WO-9627163 | A1 | 9/1996 | |
| WO | WO-9744745 | A1 | 11/1997 | |
| WO | WO-9924927 | A1 | 5/1999 | |
| WO | WO-9963886 | A1 | 12/1999 | |
| WO | WO-0060522 | A2 | 10/2000 | |
| WO | WO-0133457 | A1 | 5/2001 | |
| WO | WO-0181829 | A1 | 11/2001 | |
| WO | WO-0217075 | A2 | 2/2002 | |
| WO | WO-0233577 | A1 | 4/2002 | |
| WO | WO-02078594 | A2 | 10/2002 | |
| WO | WO-02101713 | A1 | 12/2002 | |
| WO | WO-03054668 | A2 | 7/2003 | |
| WO | WO-03094090 | A2 | 11/2003 | |
| WO | WO-2004057514 | A2 | 7/2004 | |
| WO | WO-2004074457 | A2 | 9/2004 | |
| WO | WO-2005022349 | A2 | 3/2005 | |
| WO | WO-2005031632 | A2 | 4/2005 | |
| WO | WO-2005036447 | A2 | 4/2005 | |
| WO | WO-2005045461 | A1 | 5/2005 | |
| WO | WO-2005053793 | A1 | 6/2005 | |
| WO | WO-2005057466 | A2 | 6/2005 | |
| WO | WO-2005083619 | A2 | 9/2005 | |
| WO | WO-2005101282 | A2 | 10/2005 | |
| WO | WO-2005109297 | A2 | 11/2005 | |
| WO | WO-2005120097 | A2 | 12/2005 | |
| WO | WO-2006021154 | A1 | 3/2006 | |
| WO | WO-2006066583 | A1 | 6/2006 | |
| WO | WO-2006066585 | A2 | 6/2006 | |
| WO | WO-2006071711 | A2 | 7/2006 | |
| WO | WO-2006099120 | A2 | 9/2006 | |
| WO | WO-2006108858 | A1 | 10/2006 | |
| WO | WO-2006111109 | A1 | 10/2006 | |
| WO | WO-2007027490 | A2 | 3/2007 | |
| WO | WO-2007035646 | A2 | 3/2007 | |
| WO | WO-2007127879 | A2 | 11/2007 | |
| WO | WO-2007133478 | A2 | 11/2007 | |
| WO | WO-2007137869 | A2 | 12/2007 | |
| WO | WO-2008010012 | A2 | 1/2008 | |
| WO | WO-2008036344 | A1 | 3/2008 | |
| WO | WO-2008039314 | A2 | 4/2008 | |
| WO | WO-2008062382 | A2 | 5/2008 | |
| WO | WO-2008116295 | A1 | 10/2008 | |
| WO | WO-2008150633 | A2 | 12/2008 | |
| WO | WO-2009140669 | A2 | 11/2009 | |
| WO | WO-2009151645 | A2 * | 12/2009 | ......... A61F 13/0216 |
| WO | WO-2010017484 | A2 | 2/2010 | |
| WO | WO-2010025166 | A1 | 3/2010 | |
| WO | WO-2010025467 | A1 | 3/2010 | |
| WO | WO-2010039481 | A1 * | 4/2010 | .......... A61M 1/0088 |
| WO | WO-2010078558 | A1 | 7/2010 | |
| WO | WO-2010085033 | A2 | 7/2010 | |
| WO | WO-2010132617 | A2 | 11/2010 | |
| WO | WO-2010145780 | A1 | 12/2010 | |
| WO | WO-2011005633 | A2 | 1/2011 | |
| WO | WO-2011023384 | A1 | 3/2011 | |
| WO | WO-2011039676 | A2 | 4/2011 | |
| WO | WO-2011046860 | A2 | 4/2011 | |
| WO | WO-2011047334 | A1 | 4/2011 | |
| WO | WO-2011123933 | A1 | 10/2011 | |
| WO | WO-2011137230 | A1 | 11/2011 | |
| WO | WO-2012027342 | A1 | 3/2012 | |
| WO | WO-2012027914 | A1 | 3/2012 | |
| WO | WO-2012027915 | A1 | 3/2012 | |
| WO | WO-2012051278 | A1 | 4/2012 | |
| WO | WO-2012100624 | A1 | 8/2012 | |
| WO | WO-2012127281 | A1 | 9/2012 | |
| WO | WO-2013026999 | A1 | 2/2013 | |
| WO | WO-2013036853 | A2 | 3/2013 | |
| WO | WO-2013061887 | A1 | 5/2013 | |
| WO | WO-2013102855 | A1 | 7/2013 | |
| WO | WO-2013109517 | A1 | 7/2013 | |
| WO | WO-2013138182 | A1 | 9/2013 | |
| WO | WO-2013141870 | A1 | 9/2013 | |
| WO | WO-2013155193 | A1 | 10/2013 | |
| WO | WO-2013175076 | A1 | 11/2013 | |
| WO | WO-2014015215 | A2 | 1/2014 | |
| WO | WO-2014018786 | A2 | 1/2014 | |
| WO | WO-2014075494 | A1 | 5/2014 | |
| WO | WO-2014089086 | A1 | 6/2014 | |
| WO | WO-2014100036 | A1 | 6/2014 | |
| WO | WO-2014100687 | A2 | 6/2014 | |
| WO | WO-2014106056 | A2 | 7/2014 | |
| WO | WO-2014123846 | A1 | 8/2014 | |
| WO | WO-2014133822 | A2 | 9/2014 | |
| WO | WO-2014141221 | A2 | 9/2014 | |
| WO | WO-2014145496 | A1 | 9/2014 | |
| WO | WO-2014150255 | A2 | 9/2014 | |
| WO | WO-2014151930 | A2 | 9/2014 | |
| WO | WO-2014152963 | A1 | 9/2014 | |
| WO | WO-2014189070 | A1 | 11/2014 | |
| WO | WO-2014009876 | A3 | 12/2014 | |
| WO | WO-2015019273 | A2 | 2/2015 | |
| WO | WO-2015025482 | A1 | 2/2015 | |
| WO | WO-2015026387 | A1 | 2/2015 | |
| WO | WO-2015050816 | A1 | 4/2015 | |
| WO | WO-2015078112 | A1 | 6/2015 | |
| WO | WO-2015085249 | A1 | 6/2015 | |
| WO | WO-2015091070 | A1 | 6/2015 | |
| WO | WO-2015124670 | A1 | 8/2015 | |
| WO | WO-2015132528 | A1 | 9/2015 | |
| WO | WO-2015140801 | A2 | 9/2015 | |
| WO | WO-2015143099 | A2 | 9/2015 | |
| WO | WO-2015145455 | A1 | 10/2015 | |
| WO | WO-2015156143 | A1 | 10/2015 | |
| WO | WO-2015164787 | A1 | 10/2015 | |
| WO | WO-2015179915 | A1 | 12/2015 | |
| WO | WO-2015179916 | A1 | 12/2015 | |
| WO | WO-2015179917 | A1 | 12/2015 | |
| WO | WO-2015181836 | A2 | 12/2015 | |
| WO | WO-2015187480 | A1 | 12/2015 | |
| WO | WO-2016001088 | A1 | 1/2016 | |
| WO | WO-2016006536 | A1 | 1/2016 | |
| WO | WO-2016075656 | A1 | 5/2016 | |
| WO | WO-2016108163 | A1 | 7/2016 | |
| WO | WO-2016118318 | A1 | 7/2016 | |
| WO | WO-2016120820 | A2 | 8/2016 | |
| WO | WO-2016136694 | A1 | 9/2016 | |
| WO | WO-2016141799 | A1 | 9/2016 | |
| WO | WO-2016151364 | A1 | 9/2016 | |
| WO | WO-2016160849 | A1 | 10/2016 | |
| WO | WO-2016175649 | A1 | 11/2016 | |
| WO | WO-2016178936 | A1 | 11/2016 | |
| WO | WO-2016190978 | A1 | 12/2016 | |
| WO | WO-2017001848 | A1 | 1/2017 | |
| WO | WO-2017004423 | A1 | 1/2017 | |
| WO | WO-2017027729 | A2 | 2/2017 | |
| WO | WO-2017035024 | A1 | 3/2017 | |
| WO | WO-2017053384 | A1 | 3/2017 | |
| WO | WO-2017062042 | A1 | 4/2017 | |

OTHER PUBLICATIONS

International Preliminary Report on Patentability for Application No. PCT/US2014/026692, dated Sep. 24, 2015, 16 pages.
International Preliminary Report on Patentability for Application No. PCT/US2015/057211, dated Apr. 19, 2018, 14 pages.
International Search Report and Written Opinion for Application No. PCT/US2014/026692, dated Mar. 2, 2015, 26 pages.
International Search Report and Written Opinion for Application No. PCT/US2015/057211, dated Sep. 8, 2016, 20 pages.
Invitation to Pay Additional Fees and Partial Search Report for Application No. PCT/US2015/057211, dated Jun. 8, 2016, 7 pages.
Invitation to Pay and Partial International Search Report for Application No. PCT/US2014/026692, dated Sep. 26, 2014, 9 pages.

* cited by examiner

REDUCED PRESSURE THERAPY DEVICE OPERATION AND AUTHORIZATION MONITORING

CROSS-REFERENCE TO RELATED APPLICATIONS

This application is a divisional application of U.S. application Ser. No. 15/766,213, filed Apr. 5, 2018, which is a U.S. national stage application of International Patent Application No. PCT/US2015/057211, filed Oct. 23, 2015, which claims priority to U.S. Provisional Application No. 62/238,501, filed Oct. 7, 2015, titled "SYSTEMS AND METHODS FOR APPLYING REDUCED PRESSURE THERAPY," the entirety of which is hereby incorporated by reference.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

In some embodiments, an apparatus for processing registration and usage information for a plurality of negative pressure wound therapy devices includes a memory and a computer system including computer hardware. The memory is configured to store account information for a plurality of negative wound pressure therapy devices. The computer system is in communication with the memory. The computer system is configured to: receive a registration request to register a negative wound pressure therapy device of the plurality of negative wound pressure therapy devices to an account in the account information, the account associated with a user; determine, based at least on the registration request, whether the negative wound pressure therapy device is authorized to be registered to the account; in response to determining that the negative wound pressure therapy device is not authorized to be registered to the account, perform a first exception action; in response to determining that the negative wound pressure therapy device is authorized to be registered to the account, register the negative wound pressure therapy device to the account so that data gathered by the computer system about operations of the negative wound pressure therapy device is accessible via the account; receive a usage notification for the negative wound pressure therapy device, the usage notification indicating a location of the negative wound pressure therapy device and an operation performed by the negative wound pressure therapy device; determine, based at least on the usage notification, whether the negative wound pressure therapy device is being operated at an authorized location and whether the operation performed by the negative wound pressure therapy device is an authorized operation; in response to determining that the negative wound pressure therapy device is not operated in the authorized location or that the operation performed by the negative wound pressure therapy device is not the authorized operation, perform a second exception action; and in response to determining that the negative wound pressure therapy device is operated in the authorized location and the operation performed by the negative wound pressure therapy device is the authorized operation, store in the memory an indication of performance of the operation by the negative wound pressure therapy device to the account.

In some embodiments, the apparatus of the preceding paragraph can include one or more of the following features. The computer system can be configured to receive the registration request from a user system via a computer network, and the registration request can include a first account identifier corresponding to the account and a first device identifier corresponding to the negative wound pressure therapy device. The computer system can be configured to use a look-up table comprising account identifiers and device identifiers to determine whether the negative wound pressure therapy device is authorized to be registered to the account, and the account identifiers can include the first account identifier and the device identifiers can include the first device identifier. The first exception action can include generation and transmission of a notification communication to an owner of the account or an administrator of a group that includes the account, and the notification communication can indicate that the negative wound pressure therapy device was attempted to be registered to the account and that the negative wound pressure therapy device is unauthorized to be registered to the account. The first exception action can include generation and transmission of a command message to the negative wound pressure therapy device, and the command message can instruct the negative wound pressure therapy device not to perform one or more operations. The computer system can be configured to receive the usage indication from the negative wound pressure therapy device via a computer network, and the usage notification can provide the location as a Global Positioning System (GPS) location. The computer system can be configured to use a look-up table comprising device identifiers and location identifiers to determine whether the negative wound pressure therapy device is operated at the authorized location, and the device identifiers can include a first device identifier corresponding to the negative wound pressure therapy device and the location identifiers can include a first location identifier corresponding to the authorized location. The computer system can be configured to use a look-up table comprising device identifiers and operation identifiers to determine whether the operation performed by the negative wound pressure therapy device is the authorized operation, and the device identifiers can include a first device identifier corresponding to the negative wound pressure therapy device and the operation identifiers can include a first operation identifier corresponding to the authorized operation. The second exception action can include generation and transmission of a notification communication to an owner of the account or an administrator of a group that includes the account, and the notification communication can indicate that the negative wound pressure therapy device is operated outside of the authorized location. The second exception action can include generation and transmission of a notification communication to an owner of the account or an administrator of a group that includes the account, and the notification communication can indicate that the negative wound pressure therapy device performed an unauthorized operation. The first exception action can include generation and transmission of a command message to the negative wound pressure therapy device, and the command message can instruct the negative wound pressure therapy device not to perform one or more operations. The first exception action can be the same as the second exception action.

In some embodiments, a method of operating the apparatus of any of the preceding two paragraphs is disclosed.

In some embodiments, an apparatus for applying negative pressure therapy to a wound is disclosed. The apparatus includes a source of negative pressure and a controller. The source of negative pressure is configured to be fluidically connected to a dressing configured to be placed over a wound. The source of negative pressure is configured to deliver negative pressure wound therapy to the wound. The controller is configured to: control operations of the source of negative pressure; record operation data indicative of the operations performed by the source of negative pressure; record location data corresponding to geographical locations of the source of negative pressure over time; transmit to a remote computer over a communication interface via a computer network at least some of the operation data and at least some of the location data; and vary, based at least on one or more conditions, a timing of at least one of (i) when the controller records the operation data or the location data or (ii) when the controller transmits the at least some of the operation data and the at least some of the location data.

In some embodiments, the apparatus of the preceding paragraph can include one or more of the following features. The one or more conditions can include one or more of: (i) the controller transitioning from a first mode of operation for the source of negative pressure to a second mode of operation for the source of negative pressure different from the first mode of operation, (ii) the controller connecting to a communications network, (iii) the source of negative pressure or the controller being powered by a mains power source rather than by a battery, (iv) the controller operating in a high power mode rather than a low power mode, (v) a communications network connection being enabled for the controller, (vi) the source of negative pressure or the controller being powered on or powered off, and (vii) data being gathered to the controller as a result of provision of therapy rather than being loaded to the controller from an external connection port of a housing comprising the source of negative pressure and the controller.

In some embodiments, a method of operating the apparatus of any of the preceding two paragraphs is disclosed.

BRIEF DESCRIPTION OF THE DRAWINGS

Embodiments of the present disclosure will now be described hereinafter, by way of example only, with reference to the accompanying drawings in which.

DETAILED DESCRIPTION OF SOME EMBODIMENTS

Overview

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
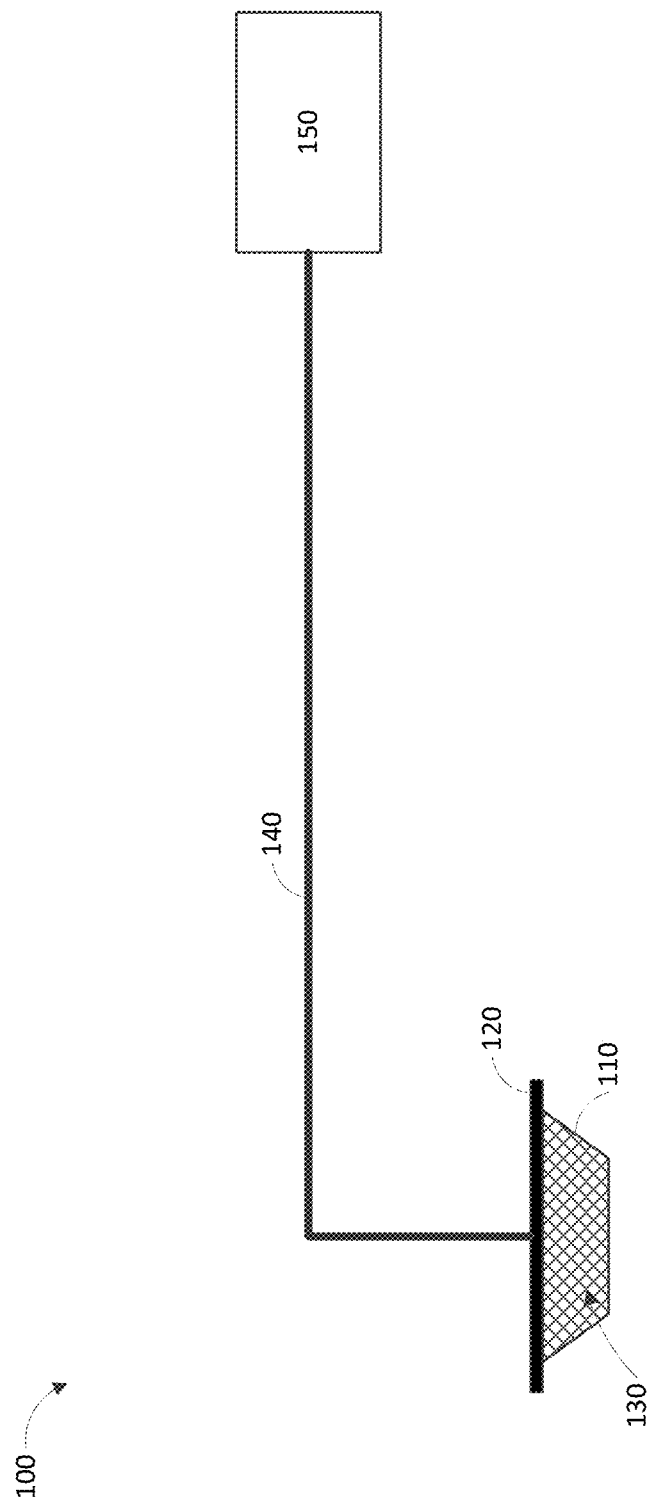
FIG. 1 illustrates a reduced pressure wound therapy system according to some embodiments.

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and conduit 140 so that the conduit 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos.

2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

Figure 2A:
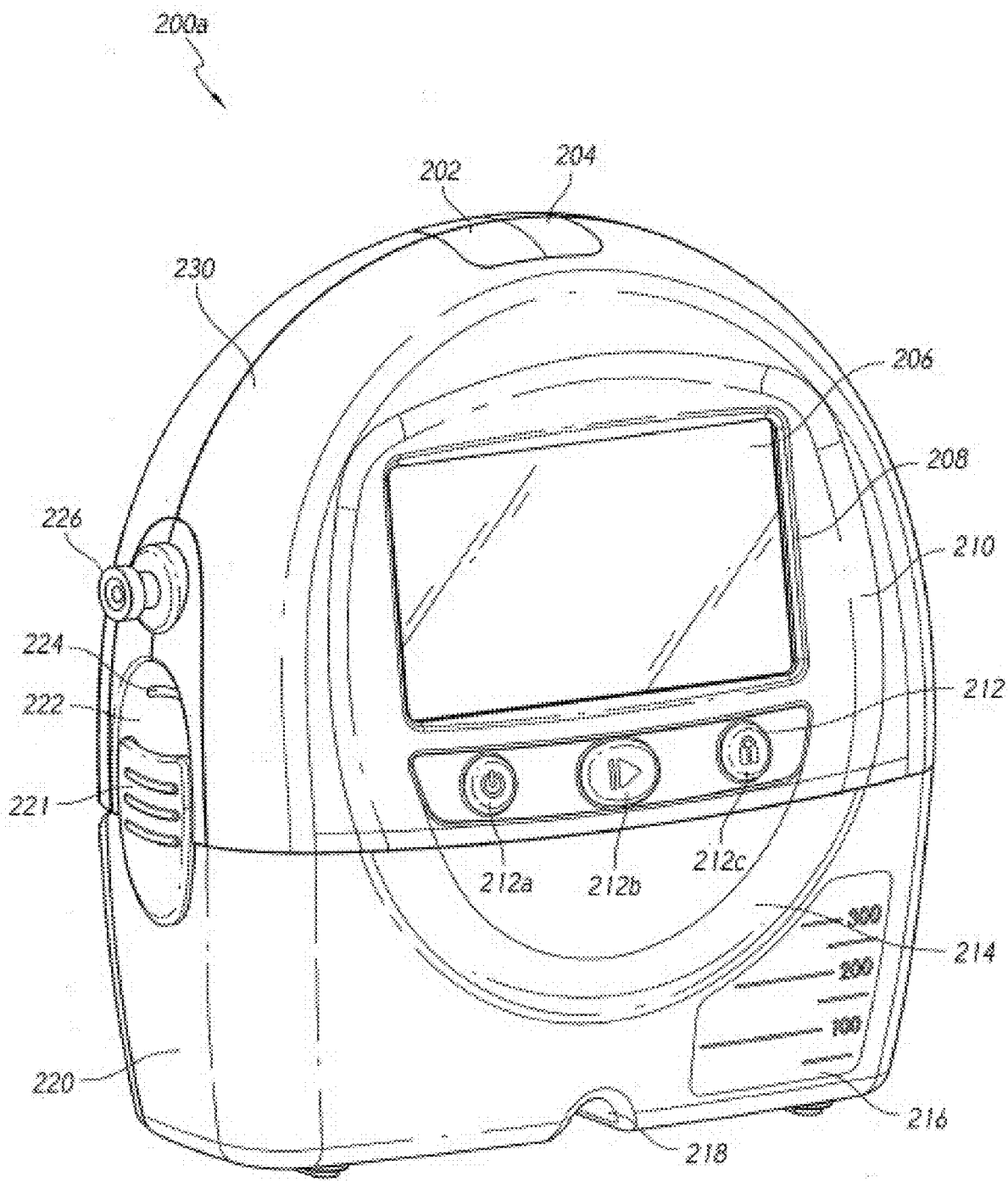
FIGS. 2A-2C illustrate a pump assembly and canister according to some embodiments.

FIG. 2A illustrates a front view 200A of a pump assembly 230, such as the pump assembly 150, and canister 220 according to some embodiments. As is illustrated, the pump assembly 230 and the canister 220 are connected, thereby forming a device. The pump assembly 230 comprises one or more indicators, such as visual indicator 202 configured to indicate alarms and visual indicator 204 configured to indicate status of the TNP system. The indicators 202 and 204 can be configured to alert a user, such as patient or medical care provider, to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw a user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. The display 206 can be a touchscreen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 comprises one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly 230 can be passed through one or more suitable filters, such as antibacterial filters. This can maintain reusability of the pump assembly 230. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted and/or various additional features are added to the canister 220. Any of the disclosed canisters may include or may omit a solidifier.

Figure 2B:
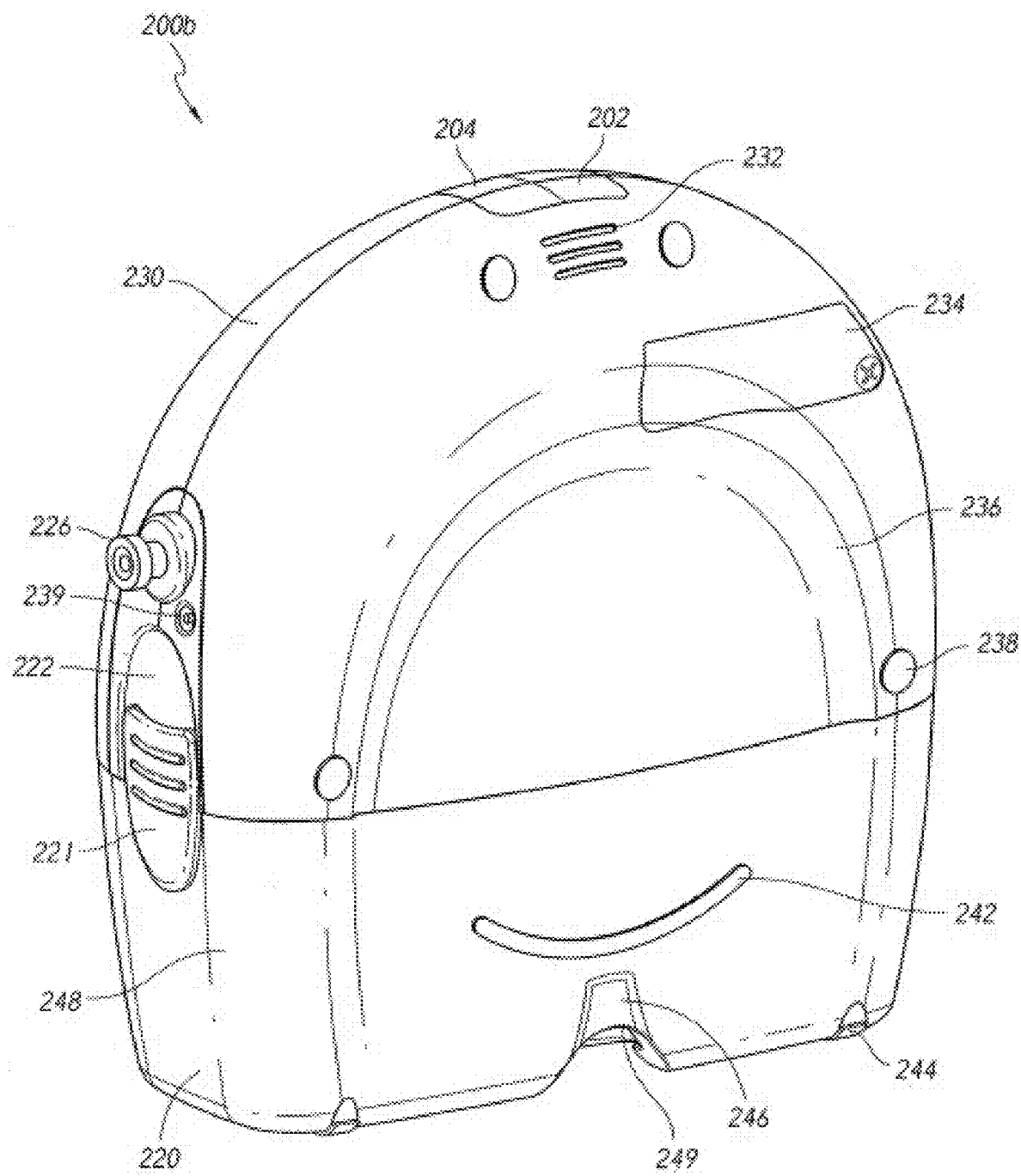

FIG. 2B illustrates a rear view 200B of the pump assembly 230 and canister 220 according to some embodiments. The pump assembly 230 comprises a speaker port 232 for producing sound. The pump assembly 230 includes a filter access door 234 for accessing and replacing one or more filters, such as antibacterial filters. The pump assembly 230 comprises a gripping portion 236 formed in the case of the pump assembly 230. The gripping portion 236 can be configured to allow the user to hold the pump assembly 230, such as during removal of the canister 220. The pump assembly 230 includes one or more covers 238 configured to as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly 230 can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
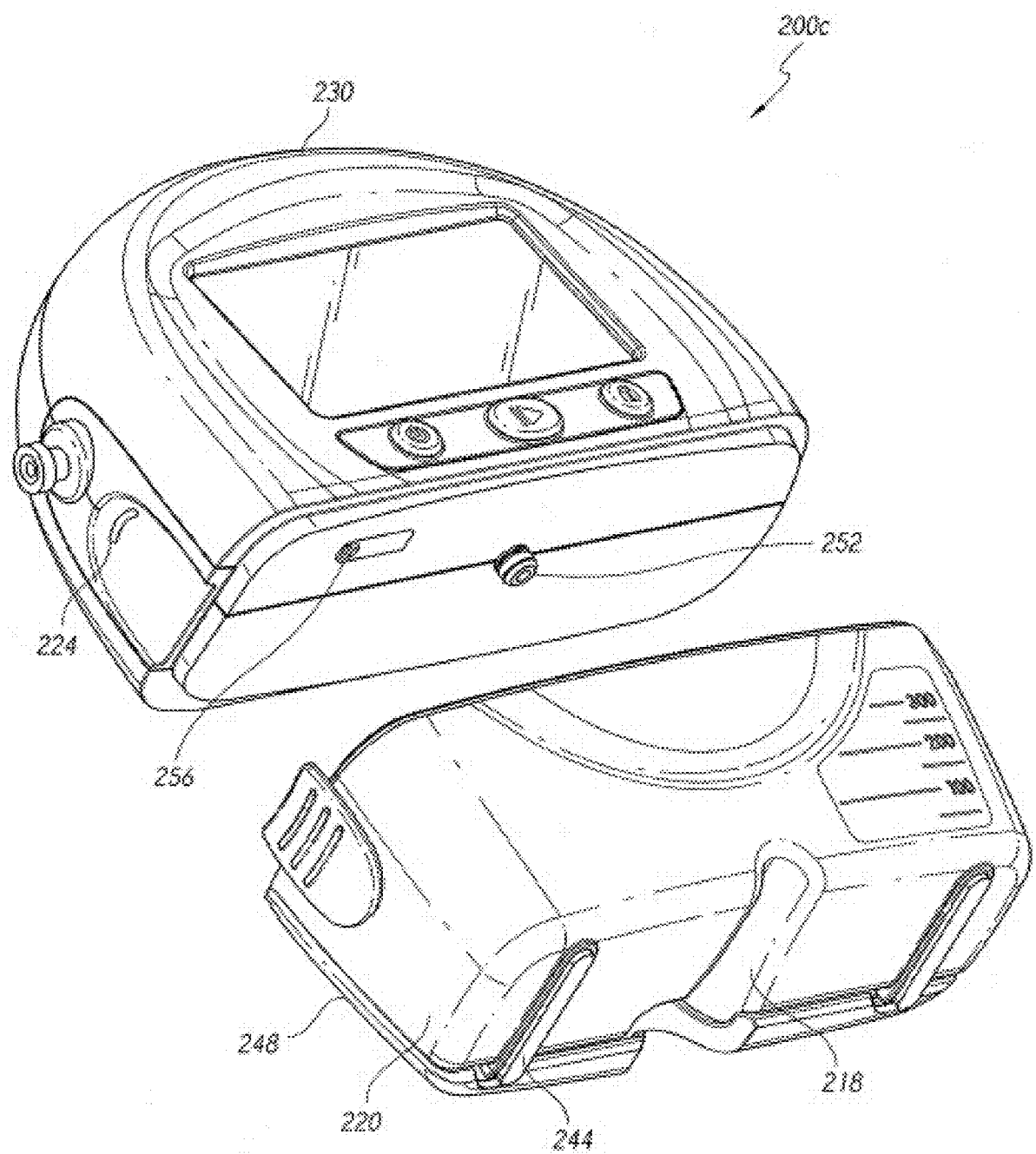

FIG. 2C illustrates a view 200C of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), DVD, FireWire, Thunderbolt, PCI Express, and the like. In other embodiments, one or more of these additional ports are accessed through the door 234.

Additional description of the pump assembly 230 is disclosed in U.S. patent application Ser. No. 14/210,062, filed on Mar. 13, 2014 and titled "SYSTEMS AND METHODS FOR APPLYING REDUCED PRESSURE THERAPY," which is incorporated by reference in its entirety.

Electronics and Software

Figure 3:
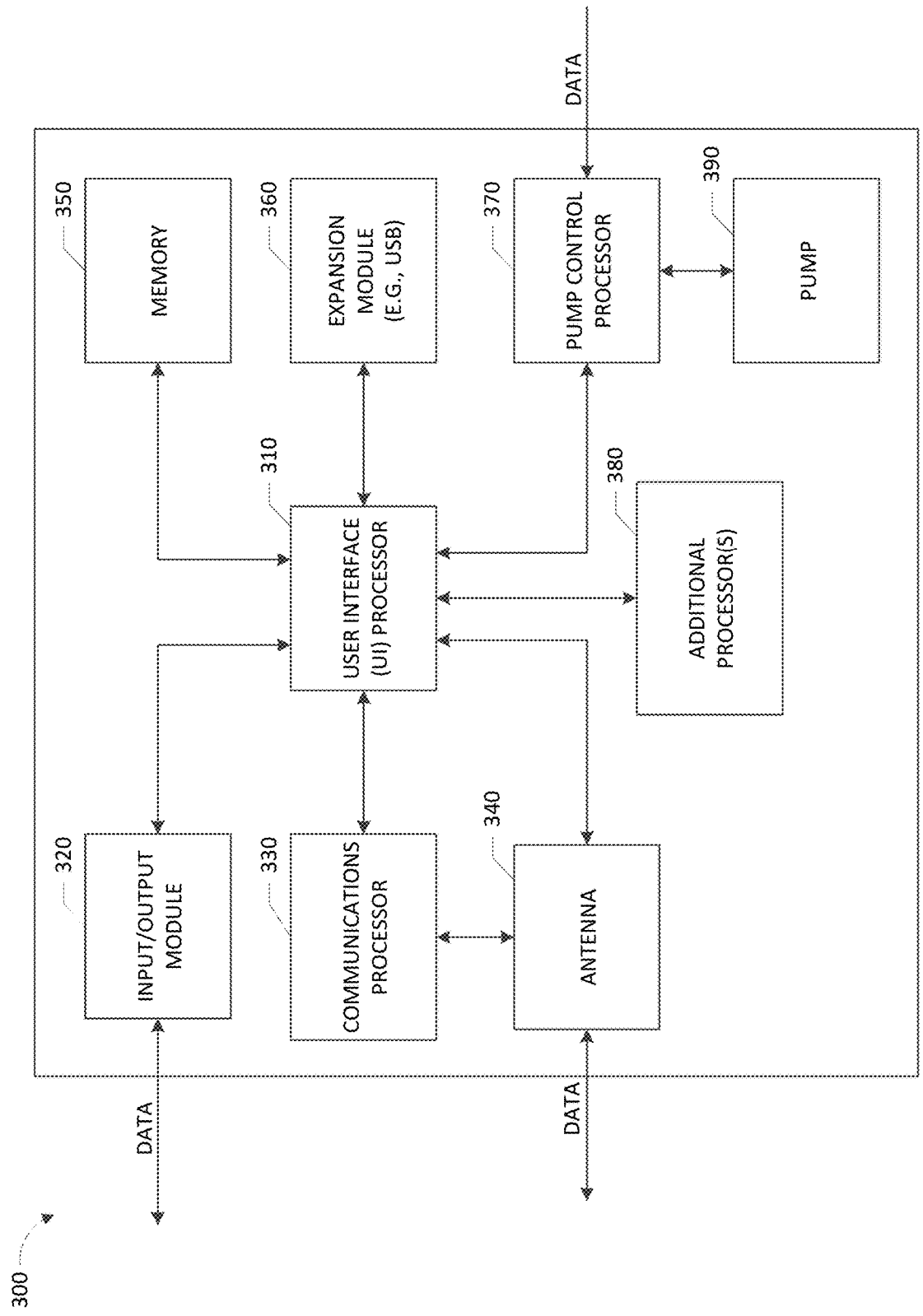
FIG. 3 illustrates an electrical component schematic of a pump assembly according to some embodiments.

FIG. 3 illustrates an electrical component schematic 300 of a pump assembly, such as the pump assembly 150, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can comprise a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump can include one or more valves, such as inlet and outlet (or exhaust) valves. The valves can be configured to open and close to enable the pump to aspirate fluid from the wound cavity 110. The pump control processor 370 can measure pressure in a fluid flow path, using data received from one or more pressure sensors, calculate the rate of fluid flow, and control the pump. The pump control processor 370 can control a pump motor so that a desired level of negative pressure is achieved in the wound cavity 110. The desired level of negative pressure can be pressure set or selected by the user. In various embodiments, the pump control processor 370 controls the pump (e.g., pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory and/or can utilize memory 350. The pump control processor 370 can be a low-power processor. In some embodiments, processor 310 is configured to control the pump 390, and pump control processor 370 is not used.

A communications processor 330 can be configured to provide wired and/or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory and/or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350. The frequency or triggering of tracking or storing the various data can moreover vary depending on one or more conditions. For example, the various data (e.g., positioning data for a pump assembly) can be tracked or stored periodically, such as once per day, hour, or minute, or with more or less frequency. As another example, the various data (e.g., positioning data for a pump assembly) can be tracked or stored when the pump assembly changes its mode of operation (e.g., initiates or stops providing therapy), connects to a communications network (e.g., 3G or WiFi network) using the communications processor 330, and the like. Such frequency or triggering control can, in certain embodiments, advantageously enable protection of the privacy of users of the pump assembly such that limited information about the use or possession of the pump assembly are tracked or stored.

In some embodiments, using the connectivity provided by the communications processor 330, the device can upload any of the data stored, maintained, and/or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Figure 4:
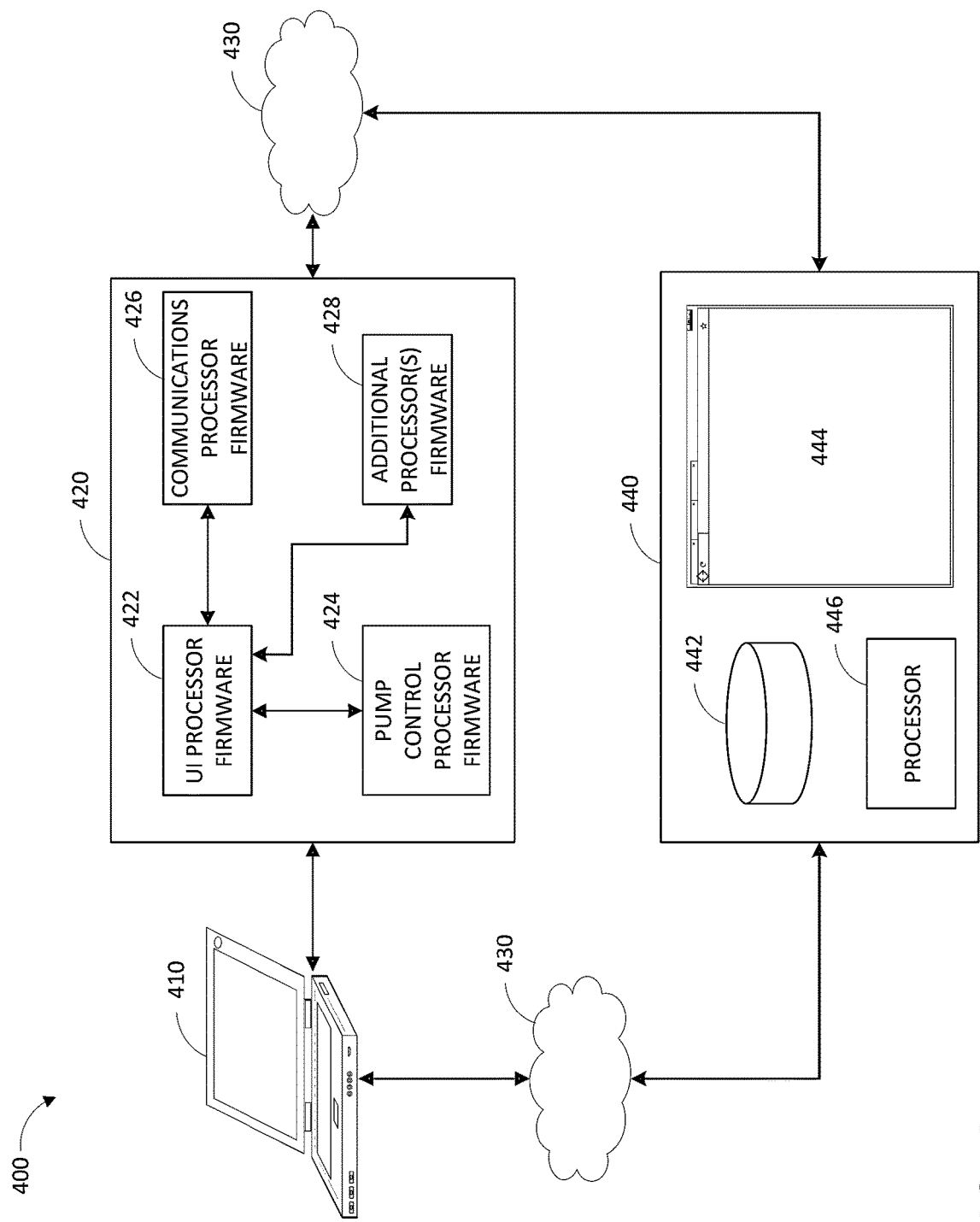
FIG. 4 illustrates a system schematic according to some embodiments.

FIG. 4 illustrates a system schematic 400 according to some embodiments. A pump assembly 420, such as the pump assembly 150, includes a user interface processor firmware and/or software 422, which can be executed by the user interface processor 310, pump control processor firmware and/or software 424, which can be executed by the pump control processor 370, communications processor firmware and/or software 426, which can be executed by the communications processor 330, and additional processor(s) firmware and/or software 428, which can be executed by one or more additional processors 380. The pump assembly 420 can be connected to a user computer 410, which can be a laptop, desktop, tablet, smartphone, and the like. A wired or wireless connection can be utilized to connect the computer 410 to the pump assembly 420. For example, a USB connection can be used. The connection between the computer 410 and the pump assembly 420 can be used for various activities, such as pump assembly location tracking, asset tracking, compliance monitoring, selection, uploading of logs, alarms, and other operational data, and adjustment of therapy settings, upgrading of software and/or firmware, and the like. The pump assembly 420 and computer 410 can communicate with a remote computer or server 440 via the cloud 430. As is used herein, the term "cloud" and the like, in addition to having its ordinary meaning, can refer to the Internet. The remote computer 440 can include a data storage module 442 and a web interface 444 for accessing the remote computer 440. The remote computer 440 includes a processor 446, such as one or more CPUs. In some embodiments, the remote computer 440 includes multiple computers.

The connection between the computer 410 and pump assembly 420 can be utilized to perform one or more of the following: initialization and programming of the pump assembly 420, firmware and/or software upgrades, maintenance and troubleshooting, selecting and adjusting therapy parameters, and the like. In some embodiments, the computer 410 can execute an application program for communicating the pump assembly 420.

The pump assembly 420 can upload various data to the remote computer (or multiple remote computers) 440 via the cloud 430. As explained above, upload data can include activity log(s), alarm log(s), therapy duration information, total therapy time, lifetime therapy information, device information, device location information, patient information, etc. In addition, the pump assembly 420 can receive and process commands received from the cloud 430.

In some embodiments, the frequency or triggering of uploading various data by the pump assembly can moreover vary depending on one or more conditions. In one example, the various data can be uploaded with a frequency that depends on whether an external power source is connected to the pump assembly (e.g., the various data can be uploaded more frequently when connected to line or mains power than when not connected to mains power) and/or certain power settings for the pump assembly (e.g., the various data can be uploaded less frequently when power settings indicate a lower power mode of operation for the pump assembly). For instance, the pump assembly can upload positioning data (i) once per hour when the pump assembly is connected to mains power and when a backlight of the touchscreen is on indicating a higher power mode of operation for the pump assembly and (ii) once per two hours when the pump assembly is not connected to mains power (e.g., pump assembly is running off battery power) or when the backlight of the touchscreen is off indicating a lower power mode of operation for the pump assembly. In another example, the various data may be uploaded when a communications network connection is enabled for the pump assembly or when the pump assembly is connected to a communications network, but not when communications network connection is disabled or when the pump assembly is not connected to the communications network. In yet another example, the powering on or off of the pump assembly can trigger the transmission of the various data, potentially with a delay in some implementations (e.g., data transmission can be triggered ten minutes after power on of a pump assembly if more than one hour has elapsed since a last power off of the pump assembly). In a further example, when data is loaded to the pump assembly (e.g., via the I/O module 320, expansion module 360, etc.) rather than collected by the pump assembly (e.g., as a result of the provision of therapy by the pump assembly), the transmission of the various data, such as the data loaded to the pump assembly, can be triggered.

In some embodiments, the computer 410 can be used to create an account with the remote computer 440 and register one or more pump assemblies to the account. The computer 410 can then, for example, be used to login to the account to access saved therapy data for the one or more registered pump assemblies, access operation instructions for the one or more registered pump assemblies, enable or control certain functionality of the one or more registered pump assemblies, and the like. The registration process can additionally enable possession or usage of the one or more registered pump assemblies to be attributed to an account owner so that any restrictions on use (e.g., use limited to specific entities, within geographic areas, or under certain contractual terms) for the one or more pump assemblies may be tracked or enforced.

Operation of the Pump Assembly

In some embodiments, the pump assembly 230 can be operated using a touchscreen interface displayed on the screen 206. Various graphical user interface (GUI) screens present information on systems settings and operations, among other things. The touchscreen interface can be actuated or operated by a finger (or a stylus or another suitable device). Tapping a touchscreen cam result in making a selection. To scroll, a user can touchscreen and hold and drag to view the selections. Additional or alternative ways to operate the touchscreen interface can be implemented, such as multiple finger swipes for scrolling, multiple finger pinch for zooming, and the like.

Figure 5A:
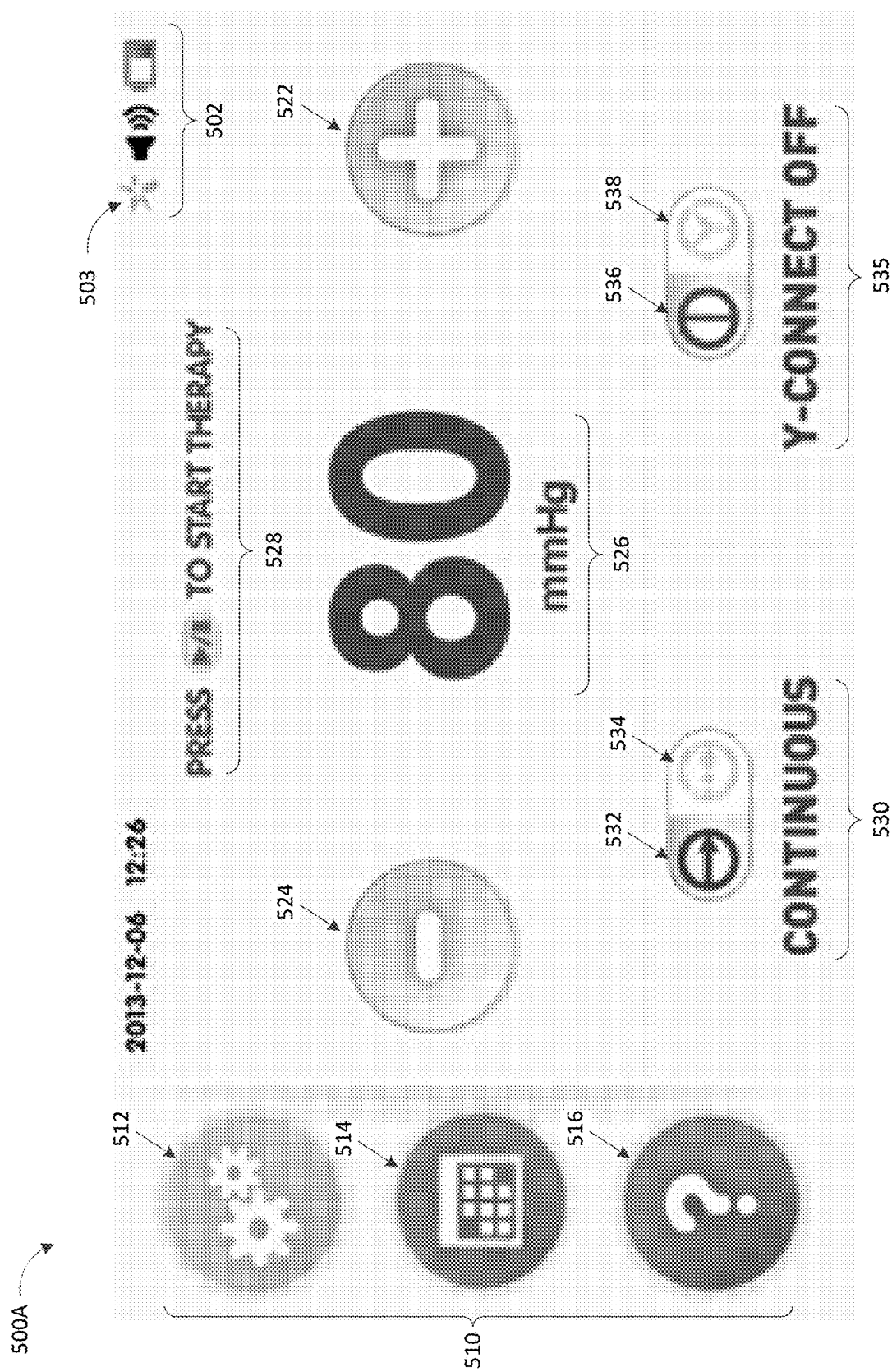
FIGS. 5A-5C illustrate graphical user interface screens according to some embodiments.
Figure 5B:
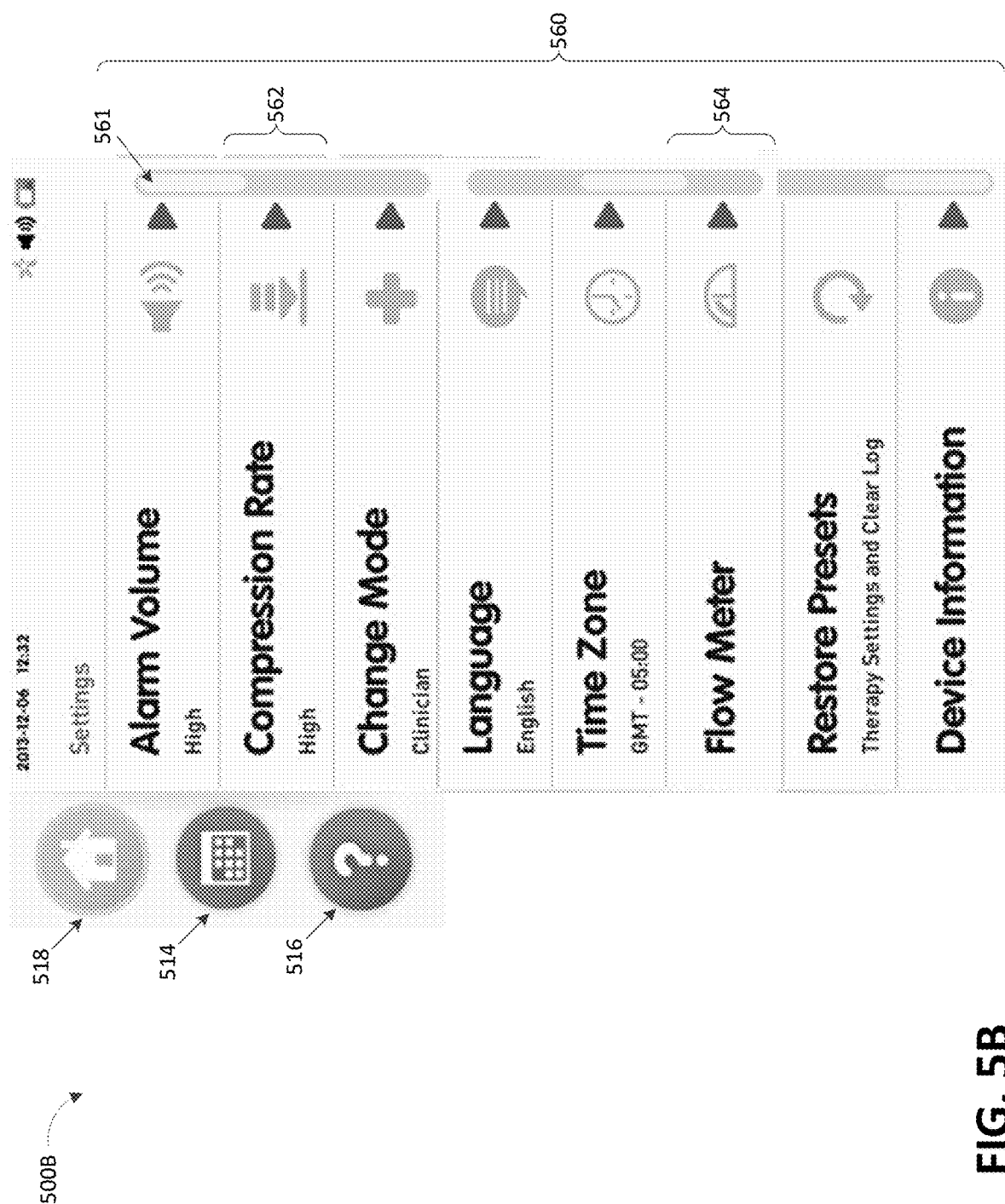
Figure 5C:
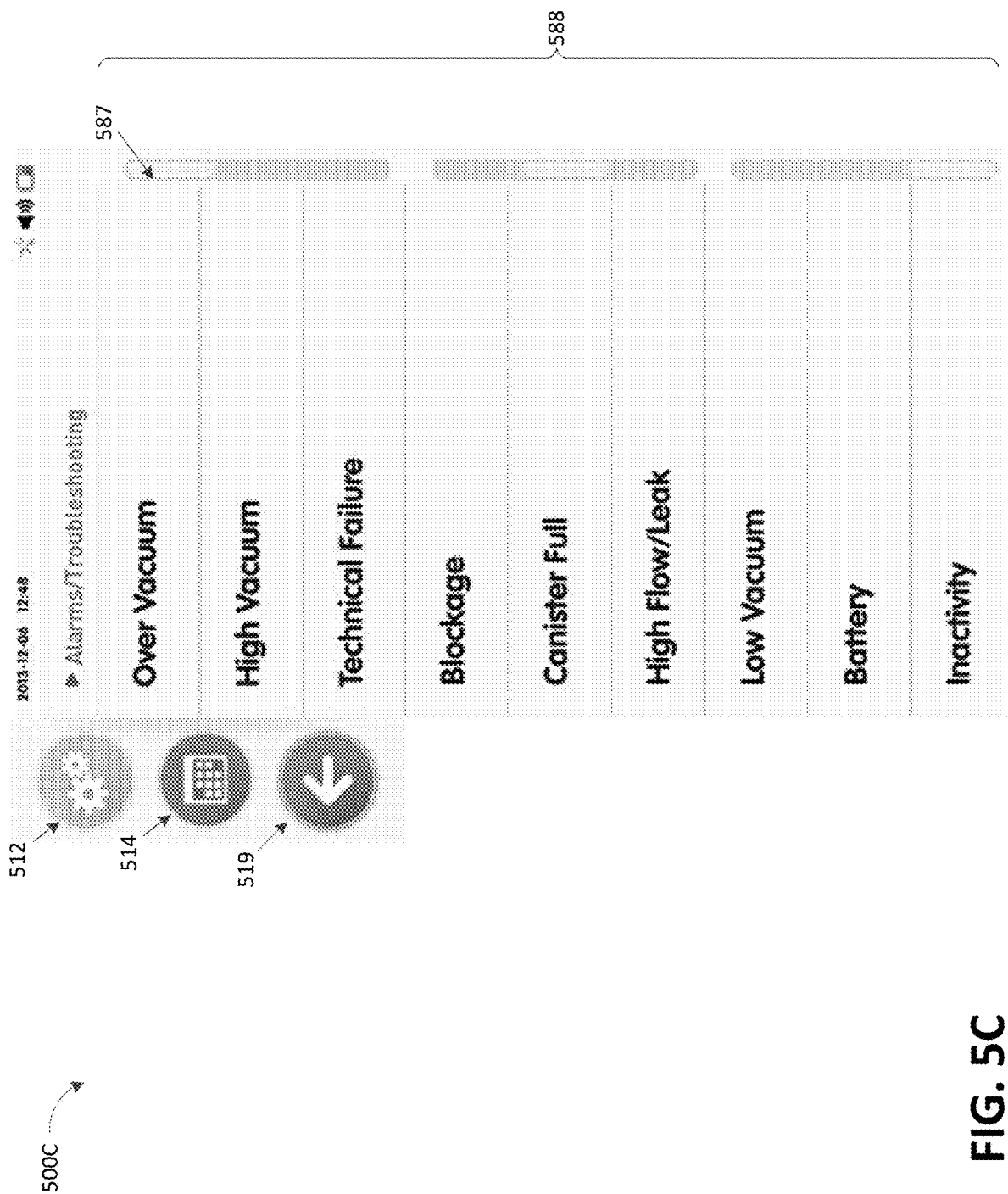

FIGS. 5A-5C illustrate graphical user interface screens according to some embodiments. The GUI screens can be displayed on the screen 206, which can be configured as a touchscreen interface. Information displayed on the screens can be generated based on input received from the user. The GUI screens can be utilized for initializing the device, selecting and adjusting therapy settings, monitoring device operation, uploading data to the network (e.g., cloud), and the like. The illustrated GUI screens can be generated directly by an operating system running on the processor 310 and/or by a graphical user interface layer or component running on the operating system. For instance, the screens can be developed using Qt framework available from Digia.

FIG. 5A illustrates a therapy settings screen 500A according to some embodiments. The therapy settings screen 500A can be displayed after the pump assembly has been initialized (e.g., screen 500A can function as a home screen). The therapy settings screen 500A includes a status bar 502 that comprises icons indicating operational parameters of the device. Animated icon 503 is a therapy delivery indicator. When therapy is not being delivered, icon 503 can be static and displayed in a color, such as gray. When therapy is being delivered, icon 503 can turn a different color, such as orange, and becomes animated, such as, rotates, pulsates, become filled with color, etc. Other status bar icons include a volume indicator and a battery indicator, and may include additional icons, such as wireless connectivity. The therapy settings screen 500A includes date/time and information. The therapy settings screen 500A includes a menu 510 that comprises menu items 512 for accessing device settings, 514 for accessing logs, 516 for accessing help, and 518 for returning to the therapy settings screen (or home screen) from other screens. The pump assembly can be configured so that after a period of inactivity, such as not receiving input from the user, therapy settings screen 500A (or home screen) is displayed. Additional or alternative controls, indicators, messages, icons, and the like can be used.

The therapy settings screen 500A includes negative pressure up and down controls 522 and 524. Up and down controls 522 and 524 can be configured to adjust the negative pressure setpoint by a suitable step size, such as ±5 mmHg. As is indicated by label 526, the current therapy selection is −80 mmHg (or 80 mmHg below atmospheric pressure). The therapy settings screen 500A includes continuous/intermittent therapy selection 530. Continuous therapy selection screen can be accessed via control 532 and intermittent therapy selection screen can be accessed via control 534. As is illustrated, the current therapy setting is to continuously deliver negative pressure at −80 mmHg. As is indicated by message 528, therapy delivery can be initiated by pressing a button, such as button 212b on the pump assembly 230. The therapy settings screen 500A includes Y-connector selection 535 for treating multiple wounds, such as two, three, etc. wounds, with one pump assembly 230. Control 536 selects treatment of a single wound, and control 538 selects treatment of more than one wound by the pump assembly. As is indicated by the label "Y-CONNECT OFF," the current selection is to treat a single wound.

Additional or alternative controls, indicators, messages, icons, and the like can be used.

FIG. 5B illustrates settings screen 500B according to some embodiments. The settings screen 500B can be accessed by selecting menu item 512 (e.g., from screen 500A). As is illustrated, settings screen 500B includes a menu 560 for adjusting various operational parameters of the pump assembly 230, including alarm volume setting, compression setting 562, user mode setting (e.g., clinician or patient), language setting, time zone setting, flow meter 564, restore presets (e.g., factory presets), and device information. Attempting to set the user mode as clinician mode may prompt the user to enter a password or satisfy any other suitable security check. Operating the pump assembly in clinician mode can provide unrestricted access to all features and settings, whereas operating the pump assembly in patient mode can prevent inadvertent changes to therapy settings by preventing access to one or more features and settings, such as therapy settings, compression settings, and the like. Alternative or additional menu items can be displayed. The illustrated menu 560 is an expanded version of the menu showing all menu items. In use, menu 560 may only partially fit on the screen, and the menu items can be accessed via the scroll bar 561 or via any other suitable alternative or additional controls. Additional or alternative controls, indicators, messages, icons, and the like can be used.

FIG. 5C illustrates alarms and troubleshooting screen 500C according to some embodiments. The screen 500C can be accessed by selecting the menu item 516 for accessing help (see FIG. 5B) and selecting alarms menu item from the help screen (not shown). As is illustrated, screen 500C includes a menu 588 with menu items for various alarm and troubleshooting categories, including over vacuum, high vacuum, blockage, canister flow, high flow/leak, and low or insufficient vacuum (as explained below) as well as technical failure (e.g., unrecoverable error), battery (e.g., low battery, critical low battery, battery failed), and inactivity (e.g., pump assembly is powered on an has been left without user interaction for longer than a certain period of time, such as 15 minutes). Alternative or additional menu items can be displayed. Accessing a particular menu item can bring up a screen with step-by-step instructions to assist in resolving the corresponding alarm. The instructions can include a combination of text, audio, video, etc. The illustrated menu 588 is an expanded version of the menu showing all menu items. In use, menu 588 may only partially fit on the screen, and menu items can be accessed via the scroll bar 587 or via any other suitable alternative or additional controls. Additional or alternative controls, indicators, messages, icons, and the like can be used.

Pump Assembly Registration and Usage Validation

Figure 6:
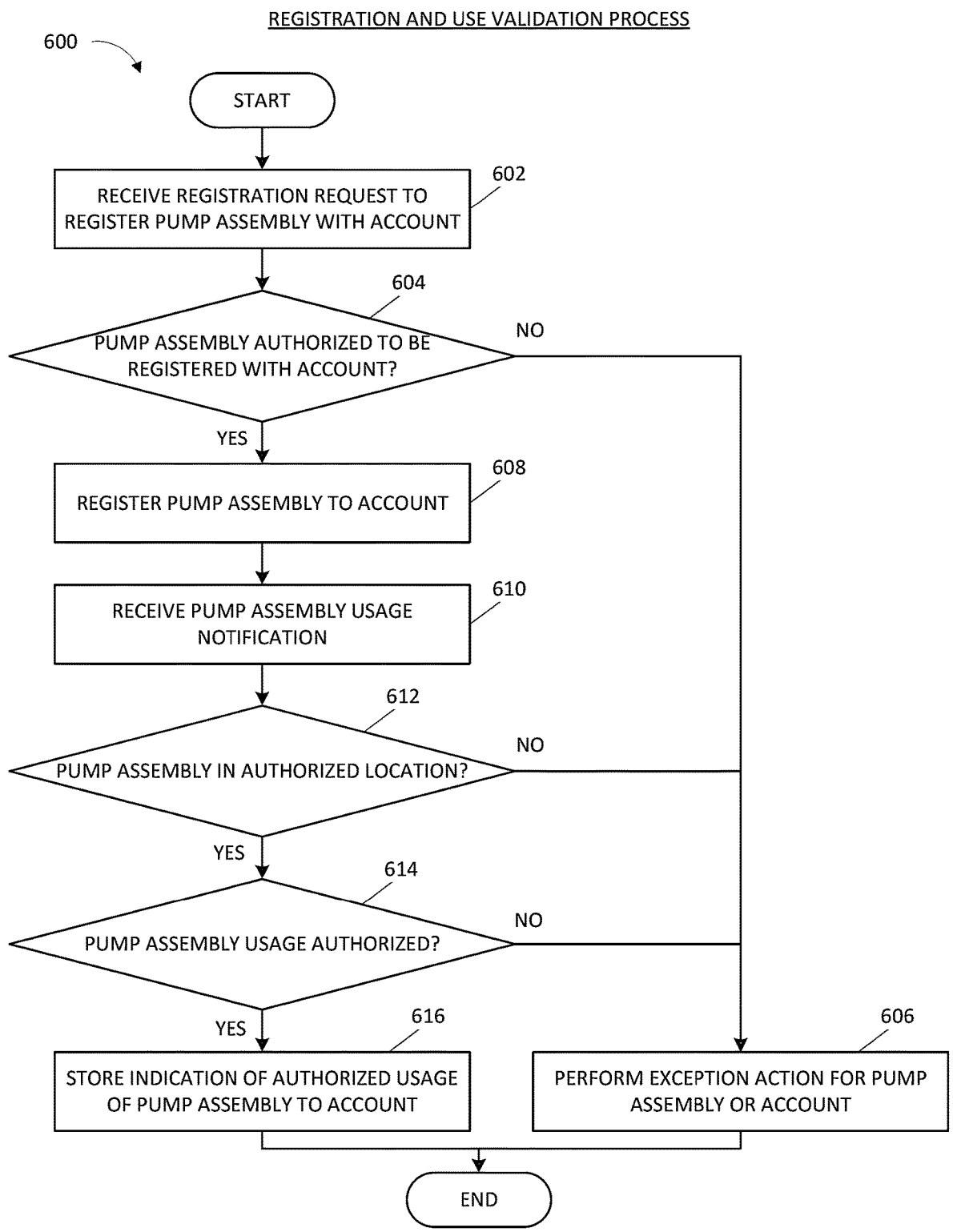
FIG. 6 illustrates a process for validating the registration and usage of a pump assembly with a remote server according to some embodiments.

FIG. 6 illustrates a process 600 for validating the registration and usage of a pump assembly, such as the pump assembly 150, with a remote server according to some embodiments. The process 600 can be executed, for example, by the remote computer 440. Advantageously, the process 600 can, in certain embodiments, enable the remote computer 440 to determine or track unauthorized registration and uses of a pump assembly and take appropriate actions (e.g., automatically generating a notification message or adjusting operation of the pump assembly). Although the process 600 is described as being performed for one pump assembly for convenience, the process 600 can be performed for tens, hundreds, thousands, or more pump assemblies.

The process 600 begins at block 602 when a registration request is received for a pump assembly, such as the pump assembly 150, to register the pump assembly to an account. The registration request can be received from a computer, such as the computer 410 or the pump assembly, such as the pump assembly 420, via a communications network, such as the cloud 430. The registration request can indicate to register the pump assembly with an account so that the pump assembly becomes associated with the account in the future. The account can be a user account or entity account in account information managed by the remote computer 440 and through which a patient, caregiver, or another individual or entity can access information gathered by the remote computer 440 related to the registered pump assembly (e.g., activity log(s), alarm log(s), therapy duration information, total therapy time, or lifetime therapy information for the registered pump assembly). One account can be registered with one or more different pump assemblies (e.g., a fleet), and one pump assembly can be registered to one or more different accounts.

At block 604, the process 600 can determine whether the pump assembly is authorized to be registered to the account. In one example, the process 600 can use a data structure (e.g., a look-up table) including account identifiers and device identifiers to determine whether an account identifier for the account and a device identifier for the pump assembly indicate that the pump assembly is authorized to be registered to the account. Other approaches for determining whether the pump assembly is authorized to be registered to the account can be used in other implementations. Pump assembly may not be authorized to be registered when it is determined that the user or entity associated with the account is not permitted to administer or be associated with the pump assembly. In response to determining that the pump assembly is unauthorized to be registered to the account, the process 600 moves to block 606.

At block 606, the process 600 performs an exception action for the pump assembly or account. The exception action can, in one example, include generating and sending a notification communication (e.g., an email, SMS, etc.) to an owner of the account or an administrator of a group (e.g., accounts within a geographic area) that includes the account informing of the exception. The notification communication can inform a receipt about the unauthorized registration attempt and/or provide suggested actions for resolving issues associated with the unauthorized registration (e.g., offering information about what steps may be taken so that the pump assembly may be successfully registered). In another example, the exception action can include preventing registration of the pump assembly to the account and/or enabling the registration to remain in effect for a limited duration (e.g., one week). In yet other examples, the exception action can include one or more of the following: (i) generating and sending a command message to the pump assembly limiting the operation capabilities for the pump assembly (e.g., disabling certain components or features, shortening the useful life, altering modes of operation, or changing data gathering approaches), (ii) generating and sending a command message to the pump assembly causing the pump assembly to provide its location (e.g., GPS location including longitude and latitude coordinates) more frequently to the remote computer 440, (iii) generating and sending a command message to the pump assembly causing the pump assembly to display a notification on the screen that the pump assembly is not properly registered (e.g., the notification may be display periodically or consistently until the pump assembly may be successfully registered), (iv) initiating the installation of revised operating or calibration software on the pump assembly, or (v) generating and sending a command message to the pump assembly causing the power of the pump assembly to cycle off and on. After block 606, the process 600 ends.

On the other hand, in response to determining that the pump assembly is authorized to be registered to the account, the process 600 moves to block 608, and the pump assembly is registered to the account. After registration, the owner of the account may login to the account to access the information gathered by the remote computer 440 related to the pump assembly, such as information communicated (e.g., uploaded) by the pump assembly.

At block 610, the process 600 receives a pump assembly usage notification. The pump assembly usage notification can be a communication (e.g., data upload) indicating that the pump assembly has been turned on or that one or more other operations have been performed by the pump assembly. The pump assembly usage notification can be communicated by the pump assembly or a computer, such as the computer 410, via a communications network, such as the cloud 430. The pump assembly usage notification can include an indication of a location of the pump assembly (e.g., a current location of the pump assembly or a location of the pump assembly when the pump assembly was turned on), as well as how, when, or for what duration the pump assembly is or was used. The indication of the location can include information such as a GPS location of the pump assembly.

At block 612, the process 600 determines whether the pump assembly is in an authorized location. The process 600 can, for instance, compare the indication of the location from the pump assembly usage notification with a permitted zone of usage for the pump assembly, such as a zone defined by terms associated with administration of the pump assembly and stored in a memory (e.g., a memory of the remote computer 440). This can be performed using a data structure (e.g., a look-up table) including device identifiers and location identifiers to determine whether a device identifier for the pump assembly and a location identifier for the location indicate that the pump assembly is or was in an authorized location. Other approaches for determining whether the pump assembly is in an authorized location can be used in other implementations.

In response to determining that the pump assembly is in an unauthorized location, the process 600 moves to block 606 and performs an exception action, such as described herein, for the pump assembly or account. For example, the exception action can include generating and sending a notification communication (e.g., an email, SMS, etc.) to an owner of an account or an administrator of a group (e.g., accounts within a geographic area) to which the pump assembly is registered or associated. The notification communication can inform a receipt about the unauthorized location for the pump assembly and/or provide suggested actions for resolving issues associated with the unauthorized location (e.g., offering information about where the pump assembly is authorized to be used or what steps may be taken so that the location in which the pump assembly may be used can be adjusted or expanded to cover the unauthorized location).

On the other hand, in response to determining that the pump assembly is in an authorized location, the process 600 moves to block 614. At block 614, the process 600 determines whether a usage of the pump assembly is authorized. The process 600, for instance, can compare the indication of how, when, or for what duration the pump assembly is or was used with an authorized usage for the pump assembly, such as a usage defined by the terms associated with usage of the pump assembly and stored in a memory (e.g., a memory of the remote computer 440). This can be performed using a data structure (e.g., a look-up table) including device identifiers and operation identifiers to determine whether a device identifier for the pump assembly and an operation identifier for an operation performed by the pump assembly indicate that the pump assembly is or was used in a permitted manner. Other approaches for determining whether the usage of the pump assembly is authorized can be utilized in other implementations.

In response to determining that the usage of the pump assembly is unauthorized, the process 600 moves to block 606 and performs an exception action, such as described herein, for the pump assembly or account. For example, the exception action can include generating and sending a notification communication (e.g., an email, SMS, etc.) to an owner of an account or an administrator of a group (e.g., accounts within a geographic area) to which the pump assembly is registered or associated. The notification communication can inform a receipt about the unauthorized usage for the pump assembly and/or provide suggested actions for resolving issues associated with the unauthorized usage (e.g., offering information about how the pump assembly may be properly used or what steps may be taken so that the pump assembly usage abilities for the pump assembly may be adjusted or expanded to cover the unauthorized usage). On the other hand, in response to determining that the usage of the pump assembly is authorized, the process 600 moves to block 616.

At block 616, the process 600 stores an indication of the authorized usage of the assembly to the account to which the pump assembly is registered. The process 600 can, for example, store to a memory (e.g., a memory of the remote computer 440) the indication of a duration of the authorized usage of the pump assembly in association with the account so that the duration of the authorized usage is later available for access via the account.

In some embodiments, the process 600 can be used or modified to track arrival of one or more pump assemblies at one or more particular locations, such as one or more hospitals, care facilities, and the like. For example, at block 610, the indication of the location for a pump assembly can be received and, based at least on the indication of the location, arrival of the pump assembly can be tracked. In various embodiments, the process 600 can be used or modified to track misplaced or lost pump assemblies. For example, the indication of the location for a pump assembly received at block 610 can be used to determine the location of a misplaced pump assembly.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method for processing registration and usage information for a plurality of negative pressure wound therapy devices, the method comprising:
   storing, in a memory device, account information for a plurality of negative pressure wound therapy devices; and
   by a computer system comprising computer hardware:
      receiving a registration request to register a negative pressure wound therapy device of the plurality of negative pressure wound therapy devices to an account in the account information, the account associated with a user;
      determining, based at least on the registration request, that the negative pressure wound therapy device is authorized to be registered to the account;
      in response to determining that the negative pressure wound therapy device is authorized to be registered to the account, registering the negative pressure wound therapy device to the account so that data gathered by the computer system about operations of the negative pressure wound therapy device is accessible via the account;
      receiving a first usage notification for the negative pressure wound therapy device, the first usage notification indicating a first location of the negative pressure wound therapy device and a first operation performed by the negative pressure wound therapy device;
      determining, based at least on a comparison of the first location to a first location identifier corresponding to an authorized location and a comparison of the first operation performed by the negative pressure wound therapy device to a first operation identifier corresponding to an authorized operation, that the negative pressure wound therapy device is being operated in a different location from the authorized location or that the first operation performed by the negative pressure wound therapy device is not the authorized operation;
      in response to determining that the negative pressure wound therapy device is being operated in the different location from the authorized location or that the first operation performed by the negative pressure wound therapy device is not the authorized operation, performing an exception action;
      receiving a second usage notification for the negative pressure wound therapy device, the second usage notification indicating a second location of the negative pressure wound therapy device and a second operation performed by the negative pressure wound therapy device;
      determining, based at least on a comparison of the second location to the first location identifier corresponding to the authorized location and a comparison of the second operation performed by the negative pressure wound therapy device to the first operation identifier corresponding to the authorized operation, that the negative pressure wound therapy device is being operated in the authorized location and that the second operation performed by the negative pressure wound therapy device is the authorized operation; and
      in response to determining that being operated in the authorized location and that the second operation performed by the negative pressure wound therapy device is the authorized operation, storing in the memory device an indication of performance of the second operation by the negative pressure wound therapy device to the account.

2. The method of claim 1, wherein the registration request is received by the computer system from a user system via a computer network, and the registration request comprises a first account identifier corresponding to the account and a first device identifier corresponding to the negative pressure wound therapy device.

3. The method of claim 2, wherein said determining that the negative pressure wound therapy device is authorized to be registered to the account comprises using a look-up table comprising account identifiers and device identifiers to determine that the negative pressure wound therapy device is authorized to be registered to the account, the account identifiers comprising the first account identifier and the device identifiers comprising the first device identifier.

4. The method of claim 1, wherein the first usage notification and the second usage notification are received from the negative pressure wound therapy device via a computer network, and the first usage notification provides the first location as a first Global Positioning System (GPS) location and the second usage notification provides the second location as a second GPS location.

5. The method of claim 1, wherein said determining that the negative pressure wound therapy device is being operated in the authorized location and that the second operation performed by the negative pressure wound therapy device is the authorized operation comprises using a look-up table comprising device identifiers and location identifiers to determine that the negative pressure wound therapy device is being operated in the authorized location, the device identifiers comprising a first device identifier corresponding to the negative pressure wound therapy device and the location identifiers comprising the first location identifier.

6. The method of claim 1, wherein said determining that the negative pressure wound therapy device is being operated in the authorized location and that the second operation performed by the negative pressure wound therapy device is the authorized operation comprises using a look-up table comprising device identifiers and operation identifiers to determine that the second operation performed by the negative pressure wound therapy device is the authorized operation, the device identifiers comprising a first device identifier corresponding to the negative pressure wound therapy device and the operation identifiers comprising the first operation identifier.

7. The method of claim 1, wherein said performing the exception action comprises generating and transmitting a notification communication to an owner of the account or an administrator of a group that includes the account, the notification communication indicating that the negative pressure wound therapy device is operated outside of the authorized location.

8. The method of claim 1, wherein said performing the exception action comprises generating and transmitting a notification communication to an owner of the account or an administrator of a group that includes the account, the notification communication indicating that the negative pressure wound therapy device performed an unauthorized operation.

9. The method of claim 1, wherein said performing the exception action comprises generating and transmitting a command message to the negative pressure wound therapy device, the command message instructing the negative pressure wound therapy device not to perform one or more operations.

10. The method of claim 1, wherein said performing the exception action comprises generating and transmitting a command message to the negative pressure wound therapy device, the command message instructing the negative pressure wound therapy device to disable one or more features.

11. The method of claim 1, wherein said performing the exception action comprises generating and transmitting a command message to the negative pressure wound therapy device, the command message instructing the negative pressure wound therapy device to increase a frequency of transmitting a location of the negative pressure wound therapy device.

12. The method of claim 1, wherein said performing the exception action comprises generating and transmitting a command message to the negative pressure wound therapy device, the command message instructing the negative pressure wound therapy device to update software of the negative pressure wound therapy device.

13. The method of claim 1, wherein said performing the exception action comprises generating and transmitting a command message to the negative pressure wound therapy device, the command message instructing the negative pressure wound therapy device to cycle power of the negative pressure wound therapy device.

14. The method of claim 1, wherein said performing the exception action comprises generating and transmitting a notification communication to an owner of the account or an administrator of a group that includes the account, the notification communication indicating that the negative pressure wound therapy device was attempted to be registered to the account and that the negative pressure wound therapy device is unauthorized to be registered to the account.

15. The method of claim 1, wherein performing the exception action comprises: performing a first exception action in response to determining that the negative pressure wound therapy device is being operated in the different location from the authorized location and performing a second exception action in response to determining that the first operation performed by the negative pressure wound therapy device is not the authorized operation.

* * * * *